(12) United States Patent
Kusumoto et al.

US009532950B2

(10) Patent No.: US 9,532,950 B2
(45) Date of Patent: Jan. 3, 2017

(54) VECTOR FOR PULMONARY DELIVERY, INDUCING AGENT, AND USES

(75) Inventors: Kenji Kusumoto, Tokushima (JP); Hideyoshi Harashima, Sapporo (JP); Hidetaka Akita, Sapporo (JP); Hiroto Hatakeyama, Sapporo (JP); Taichi Ishitsuka, Sapporo (JP)

(73) Assignees: National University Corporation Hokkaido University, Hokkaido (JP); Taiho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 14/004,942

(22) PCT Filed: Mar. 13, 2012

(86) PCT No.: PCT/JP2012/056406
§ 371 (c)(1),
(2), (4) Date: Nov. 15, 2013

(87) PCT Pub. No.: WO2012/124688
PCT Pub. Date: Sep. 20, 2012

(65) Prior Publication Data
US 2014/0079770 A1   Mar. 20, 2014

(30) Foreign Application Priority Data
Mar. 14, 2011   (JP) .................................. 2011-055765

(51) Int. Cl.
| A61K 38/00 | (2006.01) |
| A61K 9/127 | (2006.01) |
| A61K 47/48 | (2006.01) |
| A61K 31/7105 | (2006.01) |
| C12N 15/89 | (2006.01) |
| A61K 31/713 | (2006.01) |
| A61K 9/00 | (2006.01) |
| A61K 31/19 | (2006.01) |
| A61K 48/00 | (2006.01) |
| C12N 15/11 | (2006.01) |

(52) U.S. Cl.
CPC ........... *A61K 9/1271* (2013.01); *A61K 9/0019* (2013.01); *A61K 9/127* (2013.01); *A61K 31/19* (2013.01); *A61K 31/713* (2013.01); *A61K 31/7105* (2013.01); *A61K 47/48815* (2013.01); *A61K 47/48823* (2013.01); *A61K 48/005* (2013.01); *A61K 48/0008* (2013.01); *C12N 15/89* (2013.01); *A61K 48/00* (2013.01); *C12N 15/111* (2013.01); *C12N 2310/14* (2013.01); *C12N 2320/32* (2013.01)

(58) Field of Classification Search
CPC .................. A61K 38/00; C07K 1/22
See application file for complete search history.

(56) References Cited

U.S. PATENT DOCUMENTS

| 5,547,932 A | 8/1996 | Curiel |
| 5,981,273 A | 11/1999 | Curiel |
| 6,022,735 A | 2/2000 | Curiel |
| 6,077,663 A | 6/2000 | Curiel |
| 6,245,427 B1* | 6/2001 | Duzgunes ........ A61K 47/48284 |
| | | 424/9.321 |
| 6,274,322 B1 | 8/2001 | Curiel |
| 6,410,328 B1* | 6/2002 | Maclachlan et al. ......... 435/458 |
| 6,417,326 B1* | 7/2002 | Cullis .................. A61K 9/1271 |
| | | 530/324 |
| 6,743,638 B1* | 6/2004 | Tsilosani ................ G01N 33/52 |
| | | 422/68.1 |
| 2003/0125517 A1* | 7/2003 | Cullis .................. A61K 9/1271 |
| | | 530/324 |
| 2003/0203865 A1* | 10/2003 | Harvie ................. A61K 9/1272 |
| | | 514/44 R |
| 2003/0224037 A1 | 12/2003 | Eriguchi |
| 2004/0138419 A1* | 7/2004 | Zahner ................. C07K 14/005 |
| | | 530/350 |
| 2005/0025821 A1* | 2/2005 | Harvie ................. A61K 9/1272 |
| | | 424/450 |
| 2006/0240091 A1* | 10/2006 | Allon et al. ................... 424/450 |
| 2006/0281677 A1* | 12/2006 | Albarran et al. ............... 514/12 |
| 2007/0299244 A1* | 12/2007 | Chaki et al. .................. 530/303 |
| 2010/0104623 A1 | 4/2010 | Harashima |
| 2015/0140066 A1* | 5/2015 | Harashima ............. A61K 9/127 |
| | | 424/450 |

FOREIGN PATENT DOCUMENTS

| JP | H01-249717 A | 10/1989 |
| JP | H10-506001 A | 6/1998 |
| JP | 2004-010481 A | 1/2004 |

(Continued)

OTHER PUBLICATIONS

De-Kuan Chang et al., "A Novel Peptide Enhances Therapuetic Efficacy of Liposomal Anti-Cancer Drugs in Mice Models of Human Lung Cancer", PLOS ONE, vol. 4, No. 1, Jan. 12, 2009, pp. e4171.

D. Klink et al., "Gene delivery systems-gene therapy vectors for cystic fibrosis", Journal of Cystic Fibrosis, vol. 3, 1, Aug. 1, 2004, pp. 203-212.

Kentaro Sasaki et al., "An artificial virus-like nano carrier system: enhanced endosomal escape of nanoparticles via synergistic action of pH-sensitive fusogenic peptide derivatives", Analytical and Bioanalytical Chemistry, vol. 391, No. 8, Mar. 20, 2008, pp. 2717-2727.

(Continued)

*Primary Examiner* — Marcela M Cordero Garcia
(74) *Attorney, Agent, or Firm* — Rothwell, Figg, Ernst & Manbeck, P.C.

(57) ABSTRACT

The present invention provides a liposome having excellent lung migration ability that had not existed hitherto, by including GALA or Chol-GALA in the liposome. Furthermore, by using the liposome, a pulmonary delivery carrier having a stronger knockdown effect of siRNA when compared to existing carriers is provided.

14 Claims, 8 Drawing Sheets

(56) References Cited

FOREIGN PATENT DOCUMENTS

| JP | 2006-028030 A | 2/2006 |
|---|---|---|
| JP | 2007-145761 A | 6/2007 |
| WO | 2008105178 A1 | 4/2008 |
| WO | 2010067617 A1 | 6/2010 |

OTHER PUBLICATIONS

Jun Yamaguchi et al., "Comparison between a Multifunctional Envelope-Type Nano Device and Lipoplex for Delivery to the liver", Biological & Pharmaceutical Bulletin, vol. 33, No. 5, Jan. 1, 2010, pp. 926-929.

Extended European Search Report for the corresponding EP Patent Application No. 12757063.8, dated Aug. 5, 2014, 7 pages.

Kusumoto et al., "Construction of siRNA delivery system targeting lung vascular endothelial cells", Drug Delivery System, May 28, 2011, vol. 26, No. 3, p. 293.

Ukawa, Masami et al., 2-Methacryloyloxyethyl phosphorylcholine polymer (MPC)-coating improves the transfection activity of GALA-modified lipid nanoparticles by assisting the cellular uptake and intracellular dissociation of plasmid DNA in primary hepatocytes, Biomaterials, vol. 31, 2010, pp. 6355-6362—Cited in an office action dated Nov. 25, 2014 in corresponding Chinese Patent Appln. No. 201280023256.3.

Subbarao et al., "pH-Dependent Bilayer Destabilization by an Amphipathic Peptide", Biochemistry, 1987, vol. 26, No. 11, pp. 2964-2972.

Kakudo et al., "Transferrin-Modified Liposomes Equipped with a pH-Sensitive Fusogenic Peptide: An Artifical Viral-like Delivery System", Biochemistry, 2004, vol. 43, No. 19, pp. 5618-5628.

Peng et al., "Gd-DTPA-loaded polymeric micelles for high relaxivity MR cancer imaging and cancer metastasis diagnosis", Drug Delivery System, May 28, 2011, vol. 26, No. 3, p. 293.

Khalil et al., "Octaarginine- and pH sensitive fusogenic peptide-modified nanoparticles for liver gene delivery", Journal of Controlled Release, 156 (2011), pp. 374-380.

Hatakeyama et al., "A pH-sensitivie fusogenic peptide facilitates endosomal escape and greatly enhances the gene silencing of siRNA-containing nanoparticles in vitro and in vivo", Journal of Controlled Release, 139 (2009) pp. 127-132.

Ishitsuka et al., "Functional improvement of an IRQ-PEG-MEND for delivering genes to the lung", Journal of Controlled Release, 154 (2011) pp. 77-83.

\* cited by examiner figure 1-A
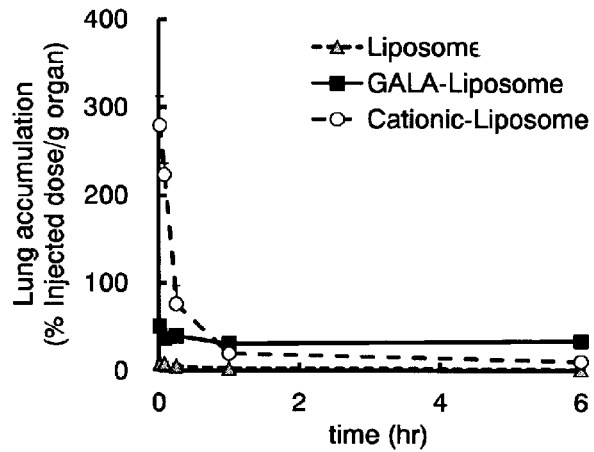
figure 1-B
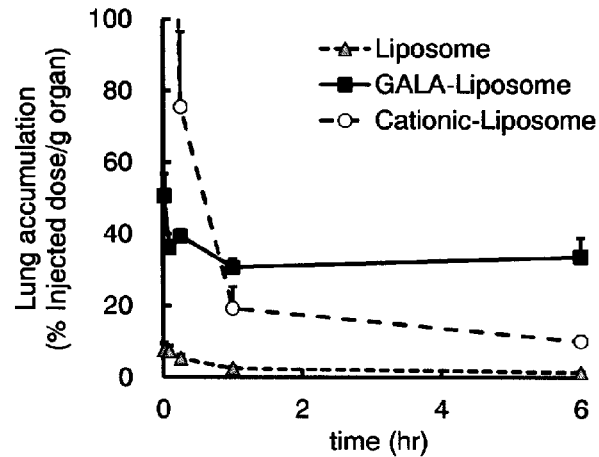
figure 2
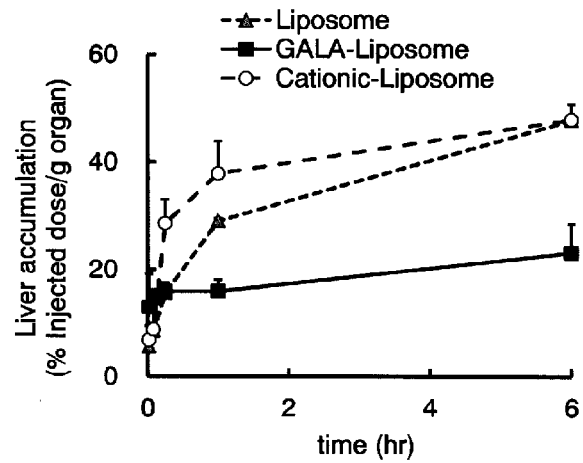

figure 5
MEND1                            GALA-MEND1
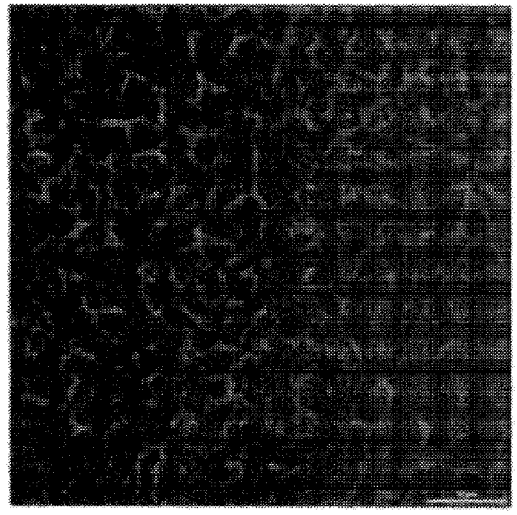 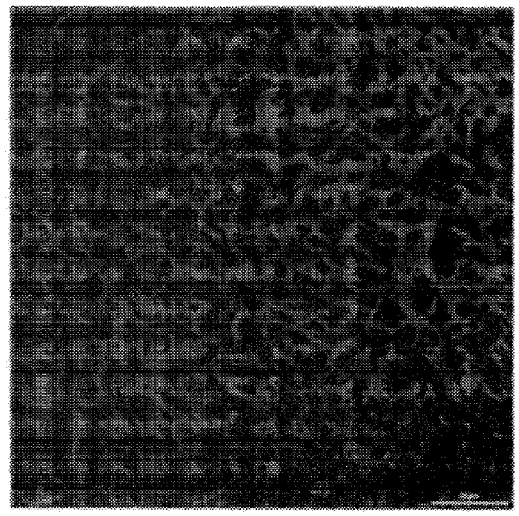
Red: siRNA (Cy5)
Blue: Vascular endothelial cell(FITC-isolectin)
Scale bar: 50 μm
figure 6
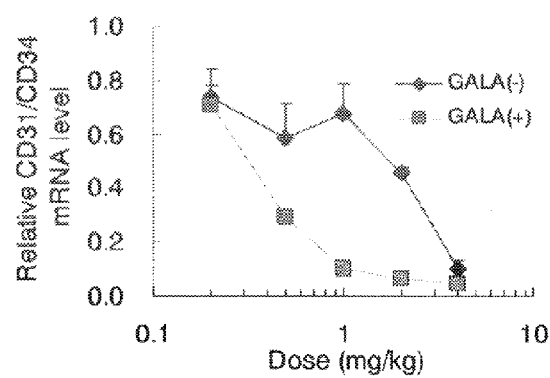

MEND characteristics

VECTOR FOR PULMONARY DELIVERY, INDUCING AGENT, AND USES

CROSS REFERENCE TO RELATED APPLICATION

This application is a 35 U.S.C. 371 National Phase Entry Application from PCT/JP2012/056406, filed Mar. 13, 2012, which claims the benefit of Japan Patent Application No. 2011-055765 filed on Mar. 14, 2011, the disclosure of which is incorporated herein in its entirety by reference.

The present application includes a Sequence Listing filed in electronic format. The Sequence Listing is entitled "2941-206_ST25.txt" created on Nov. 13, 2013, and is 4,000 bytes in size. The information in the electronic format of the Sequence Listing is part of the present application and is incorporated herein by reference in its entirety.

TECHNICAL FIELD

The present invention relates to an introduction agent and a vector for pulmonary delivery, and uses thereof.

CROSS REFERENCE TO RELATED APPLICATION

The present application claims the benefit of priority to Japan Patent Application No. 2011-55765 filed on Mar. 14, 2011 (the entirety thereof is incorporated herein by reference).

BACKGROUND ART

In recent years, development is actively conducted for a liposome having a functional molecule introduced on the outer surface of the liposomal membrane to be used as a vector for delivering, to a target site, an intended substance such as low-molecular-weight medicines, nucleic acid medicines, antibody drugs, peptides, proteins, sugars, etc. In the field of biomedicine, research on nucleic acid medicines is actively conducted as a next-generation biomedicine that follows the footsteps of antibody drugs and protein medicines. Examples of nucleic acid medicines include antisenses, ribozymes, aptamers, decoy oligos, and siRNAs. Although clinical application of nucleic acid medicines is still in its early stage, siRNA has gathered attention in particular, and clinical tests thereof have been conducted by pharmaceutical companies and ventures in western countries. However, most of such clinical tests are limited to local administration. Although clinical tests are conducted for systemic administration using a delivery system, those have been limited to some organs expected to exhibit passive accumulation, such as the liver. Therefore, in order to expand the application range of a nucleic acid medicine represented by siRNA, there is a demand to establish a delivery system capable of active-targeting.

Examples of such a delivery system that has been developed include a liposome having a hydrophilic polymer (e.g., polyalkylene glycols such as polyethylene glycol) introduced on the outer surface of liposomal membrane (cf. Patent Literature 1 and Patent Literature 2). With this liposome, tropism of the liposome against tumor cells can be improved as a result of improvement in-blood retentivity of the liposome. Furthermore, multifunctional envelope-type nano device (MEND) (hereinafter, may be abbreviated as "MEND") has been proposed, and this device can be used as a drug delivery system for selectively delivering a gene or a peptide into specific cells.

In addition, a liposome obtained by introducing GALA on the outer surface of the liposomal membrane using cholesterol bound with GALA has been developed (cf. Non-Patent Literature 1). When a liposome undergoes endocytosis, the liposome becomes included within an endosome, and the liposome within the endosome is degraded when the endosome fuses with a lysosome. However, with the above described liposome, a substance encapsulated in the liposome can escape from the endosome and can be released in the cytoplasm.

GALA is an oligopeptide formed from 30 amino acid residues of basically a repetitive sequence of glutamic acid, alanine, leucine, and alanine (EALA). GALA was synthesized by a research group of Szoka et al. (cf. Non-Patent Literature 2), and various studies have been conducted thereon hitherto. It is known that although GALA takes a random coil structure due to electric repulsion by glutamic acid under a neutral pH condition, GALA takes an alpha helix structure having high affinity with lipid membrane through resolving of the electrical repulsion under an acidic condition (cf. Non-Patent Literature 2).

Furthermore, GALA has been used as a pH responsive endosome-escape promotion element for improving MEND activity, since, when the surface of MEND is modified with a cholesterol (Chol)-bound GALA (Chol-GALA), an endosomal membrane and a MEND lipid membrane undergo membrane fusion under an acidic condition within the endosome, resulting in a release of an encapsulated substance into the cytoplasm (cf. Patent Literature 3).

As described above, although GALA has been used as a functional element for the purpose of improving intracellular kinetics, it is not known as a lung migratory element.

Furthermore, although lung is mentioned as a target organ of a certain type of liposome modified with an endosome soluble peptide (cf. Patent Literature 4), the configuration of the peptide described therein is largely different from the configuration of the GALA peptide according to the present application formed basically from a repetitive sequence of glutamic acid, alanine, leucine, and alanine (EALA). In addition, there is no disclosure or suggestion regarding a liposome modified with the peptide migrating specifically to the lung.

CITATION LIST

Patent Literature

PTL 1: JP1-249717A
PTL 2: JP2004-10481A
PTL 3: JP2006-28030A
PTL 4: JP10-506001A

Non-Patent Literature

NPL 1: T. Kakudo et al., Biochemistry, 2004; 43: 5618-5623
NPL 2: N. K. Subbarao et al., Biochemistry, 1987; 26: 2964-2972

SUMMARY OF INVENTION

Technical Problem

An object of the present invention is to provide a technology for specifically delivering an intended substance to the lung.

It is also an object of the present invention to provide a vector that has excellent storage stability and/or does not or mostly does not aggregated after being stored for a certain period of time.

Solution to Problem

The present inventors have conducted research for a carrier having a function of causing an intended substance such as a medication to migrate to the lung with high efficiency. As a result, they discovered that a GALA peptide shows high lung migratability and perfected the present invention.

In addition, they also discovered that the lung specific migratability does not disappear even when a vector (e.g., liposome modified with a GALA peptide-lipid) including the GALA peptide is modified with PEG, and perfected the present invention.

Furthermore, they discovered that adding a helper lipid to the liposome modified with a GALA peptide or a GALA peptide-lipid allows the liposome to have physical properties of excellent storage stability and/or not aggregating or mostly not aggregating after being stored for a certain period of time; and perfected the present invention.

Thus, the present invention provides the following use, substance introduction agent, and vector.

Item 1. A use of a GALA peptide represented by SEQ ID NO: 1 as a lung migratory element of a vector for delivering an intended substance to a lung.

Item 2. The use according to item 1, wherein the GALA peptide is bound to a component of the vector.

Item 3. The use according to item 1 or 2, wherein the vector includes a lipid and/or cholesterol, and the GALA peptide is bound to a cationic lipid and/or cholesterol.

Item 4. The use according to item 1 or 2, wherein the vector includes a cationic lipid and/or cholesterol, and the GALA peptide is bound to a cationic lipid and/or cholesterol.

Item 5. A substance introduction agent whose target is a lung, the agent having an intended substance encapsulated in a vector, and the vector including a GALA peptide represented by SEQ ID NO: 1.

Item 6. The substance introduction agent according to item 5, wherein the GALA peptide is bound to a component of the vector.

Item 7. The substance introduction agent according to item 5 or 6, wherein the vector includes a lipid and/or cholesterol, and the GALA peptide is bound to a cationic lipid and/or cholesterol.

Item 8. The substance introduction agent according to item 5 or 6, wherein the vector includes a cationic lipid and/or cholesterol, and the GALA peptide is bound to a cationic lipid and/or cholesterol.

Item 9. The substance introduction agent according to any one of items 5 to 8, wherein the vector is modified with a hydrophilic polymer selected from the group consisting of polyalkylene glycol, dextran, pullulan, ficoll, polyvinyl alcohol, styrene-maleic anhydride alternating copolymer, divinyl ether-maleic anhydride alternating copolymer, amylose, amylopectin, chitosan, mannan, cyclodextrin, pectin, and carrageenan.

Item 10. The substance introduction agent according to any one of items 5 to 9, wherein the intended substance is a bioactive substance that acts on a lung.

Item 11. The substance introduction agent according to any one of items 5 to 10, wherein the intended substance is selected from the group consisting of drugs, nucleic acids, peptides, proteins, sugars, and complexes thereof.

Item 12. The substance introduction agent according to any one of items 5 to 11, the intended substance is a double-stranded RNA (dsRNA) selected from the group consisting of meroduplex RNA (mdRNA), nicked dsRNA (ndsRNA), gapped dsRNA (gdsRNA), short interfering nucleic acid (siNA), siRNA, micro RNA (miRNA), short hairpin RNA (shRNA), short interfering oligonucleotide, substituted short interfering oligonucleotide, modified short interfering oligonucleotide, chemically modified dsRNA, and post transcriptional gene silencing RNA (ptgsRNA).

Item 13. The substance introduction agent according to item 11 or 12, wherein the intended substance is a nucleic acid, and the substance introduction agent includes polyethyleneimine (PEI) in addition to the nucleic acid.

Item 14. A vector for delivering an intended substance to a lung, the vector comprising a GALA peptide represented by SEQ ID NO: 1 as an element for selectively delivering a substance to a lung.

Item 15. The vector according to item 14, wherein the vector includes a lipid and/or cholesterol, and the GALA peptide is bound to a cationic lipid and/or cholesterol.

Item 16. The vector according to Item 14, wherein the vector includes a cationic lipid and/or cholesterol, and the GALA peptide is bound to a cationic lipid and/or cholesterol.

Item 17. The vector according to item 15 or 16, wherein the vector includes a cationic lipid, and the cationic lipid includes at least one type selected from the group consisting of DOTMA, DSTAP, and DODAP.

Item 18. The vector according to any one of items 14 to 17, wherein the vector is modified with a hydrophilic polymer selected from the group consisting of polyalkylene glycol, dextran, pullulan, ficoll, polyvinyl alcohol, styrene-maleic anhydride alternating copolymer, divinyl ether-maleic anhydride alternating copolymer, amylose, amylopectin, chitosan, mannan, cyclodextrin, pectin, and carrageenan.

Item 19. The vector according to item 18, wherein polyalkylene glycol is PEG (preferably PEG having a molecular weight of 2000).

Item 20. The vector according to any one of items 14 to 19, further comprising a helper lipid.

Item 21. The vector according to item 20, wherein the helper lipid is EPC, DOPC, DOPE, or SOPE.

Item 22. The vector according to item 14, wherein the vector is a liposome, and a composition of the liposome is cationic lipid/Chol/helper lipid/STR-PEG/Chol-GALA or helper lipid/Chol/STR-PEG/Chol-GALA (more preferably a cationic lipid selected from DOTMA, DODAP, or DSTAP/Chol/a helper lipid selected from EPC, DOPE, or SOPE/STR-PEG/Chol-GALA, or EPC/Chol/STR-PEG/Chol-GALA; and further preferably DOTMA/Chol/EPC/STR-PEG/Chol-GALA, DODAP/Chol/EPC/STR-PEG/Chol-GALA, DSTAP/Chol/EPC/STR-PEG/Chol-GALA, DOTMA/Chol/DOPE/STR-PEG/Chol-GALA, DOTMA/Chol/SOPE/STR-PEG/Chol-GALA, or EPC/Chol/STR-PEG/Chol-GALA).

Item 23. The vector according to item 14, wherein: the vector is a liposome including, as a component of lipid membrane, DOTMA, Chol, and EPC;

a lipid composition (molar ratio) of the liposome regarding DOTMA/Chol/EPC is 10 to 50/20 to 50/20 to 70; and the liposome further includes STR-PEG2000 by 1 to 15 mol % and Chol-GALA by 0.1 to 5 mol % with respect to the total lipid amount of DOTMA/Chol/EPC.

Item 24. A method for introducing an intended substance to a lung, the method comprising administering, to a mammal, a vector that has encapsulated therein the intended substance and has bound thereto a GALA peptide represented by SEQ ID NO: 1.

Item 25. A therapeutic method for treating lung cancer, the method comprising administering, to a mammal having lung cancer, a vector that has encapsulated therein an anticancer agent and has bound thereto a GALA peptide represented by SEQ ID NO: 1.

Item 26. The therapeutic method according to item 24, wherein the lung cancer is a cancer metastasized to a lung.

Item 27. A lung cancer therapeutic agent comprising a vector that has encapsulated therein an anticancer agent and has bound thereto a GALA peptide represented by SEQ ID NO: 1.

Item 28. The lung cancer therapeutic agent according to item 27, wherein the lung cancer is a cancer metastasized to a lung.

Item 29. The use according to item 3, the substance introduction agent according to item 7, or the vector according to item 15, wherein the GALA peptide is bound to a lipid component in a range of 1 to 4 mol % with respect to a total lipid amount.

Advantageous Effects of Invention

With the present invention, a vector or a substance introduction agent, particularly a liposome, for specifically delivering an intended substance to a lung is provided. Furthermore, the vector or the substance introduction agent, particularly the liposome, of the present invention can migrate to the lung and also suppress migration thereof to the liver, which is the main accumulation organ. Furthermore, the vector or the substance introduction agent, particularly the liposome, of the present invention has shown a knockdown effect surpassing that of existing siRNA delivery carriers particularly in the lung, and has demonstrated to have extremely superior introduction effect for an intended substance.

Since the vector and the substance introduction agent including the GALA peptide used in the present invention do not have the problem of aggregation, they will not block blood vessels.

BRIEF DESCRIPTION OF DRAWINGS

FIG. 1-A shows an evaluation result of lung migration of a GALA-modified liposome over time.

FIG. 1-B is a graph in which the vertical axis in FIG. 1-A is scaled up.

FIG. 2 shows an evaluation result of liver migration of a GALA-modified liposome over time.

FIG. 5 shows the result of tail-vein intravenous administration of a GALA-modified MEND encapsulating fluorescent labeled siRNA, and evaluating localization of the GALA-modified MEND in the lung 1 hour after administration using a confocal laser scanning microscope.

FIG. 6 shows the result of tail-vein intravenous administration of a GALA-modified MEND and a GALA-unmodified MEND, and evaluating the respective knockdown effects of the GALA-modified MEND and the GALA-unmodified MEND in the lung 24 hours after administration using qRT-PCR.

DESCRIPTION OF EMBODIMENTS

Figure 3:
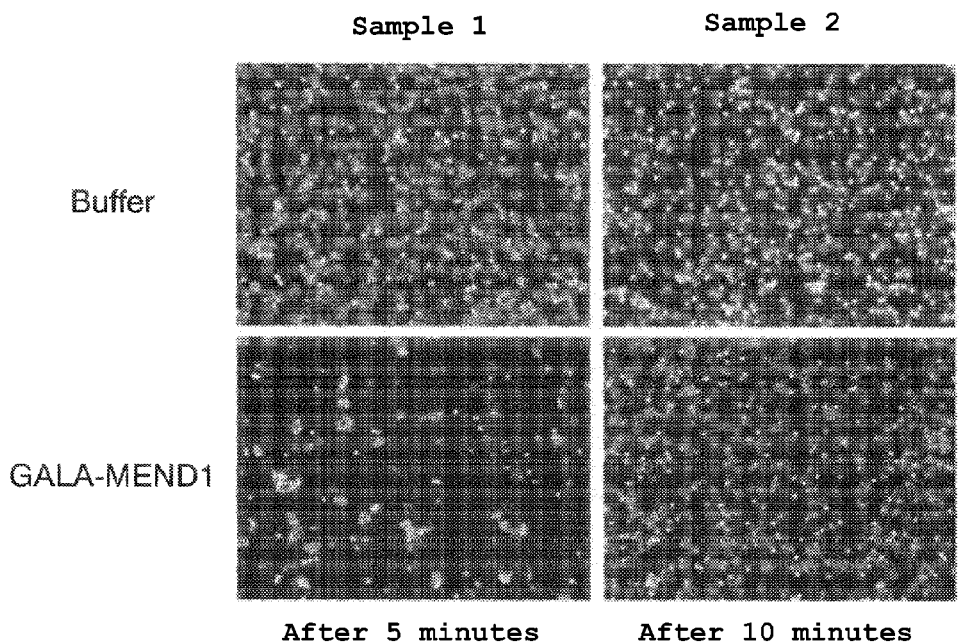
FIG. 3 shows the result of mixing blood and a GALA-modified MEND at various ratios to evaluate interaction thereof with hemocyte components.

Details of the present invention will be described in the following.

A vector of the present invention can achieve selective migration to the lung by including a GALA peptide.

A "GALA peptide represented by SEQ ID NO: 1" is a 30-amino acid peptide described below.

Ala Ala Leu Ala Glu Leu Ala Glu Ala Leu Ala Glu Ala Leu His Glu Ala Leu Ala Glu Ala Leu Ala Glu Ala Leu Ala Ala Glu Trp (SEQ ID NO: 1)

The peptide represented by SEQ ID NO: 1 has, in its sequence, 4 units of a partial structure of glutamic acid (E)-alanine (A)-leucine (L)-alanine (A). The peptide represented by SEQ ID NO: 1 may have amino acid deletion, substitution, or addition in the parts other than the partial structure, while maintaining preferably 3 units or 4 units, more preferably 4 units, of the partial structure. These modified GALA peptides are also included in the "GALA peptide represented by SEQ ID NO: 1" of the present invention.

With regard to the number and position of the deletion, substitution, or addition of amino acid made to the amino acid sequence represented by SEQ ID NO: 1; the number of amino acid is one or more, preferably 1 or several. Specific ranges thereof include: for a deletion, ordinarily 1 to 4, preferably 1 to 3, further preferably 1 or 2; for a substitution, ordinarily 1 to 6, preferably 1 to 4, further preferably 1 or 2; and for an addition, ordinarily 1 to 12, preferably 1 to 6, further preferably 1 to 4. The substitution of amino acid is preferably a substitution within analogous amino acids, such as hydrophobic amino acids (Leu, Val, Ile, Ala), aromatic amino acids (Phe, Tyr, Trp), basic amino acids (Arg, Lys, His), acidic amino acids (Glu, Asp), neutral amino acids (Gly, Ser, Thr, Cys, Met, Gln, Asn, Pro). It should be noted that, in the present specification, a GALA peptide is sometimes referred simply as "GALA."

A bond is preferably formed between the GALA peptide and a component forming the vector. Examples of the components forming the vector include lipids, proteins or peptides, sugar chains, water soluble or water miscible polymers (neutral, cationic, or anionic), surfactants, and the like. Although examples of the bond include any bond such as covalent bond, ionic bond, hydrogen bond, and coordinate bond; covalent bond or coordinate bond is preferable and covalent bond is most preferable.

The GALA peptide is included in a carrier (vector) capable of introducing a substance to a cell. Examples of the carrier (vector) capable of introducing a substance to a cell include lipid based transfection reagents, virus derived particles, liposomes, polyplexes, micelles, and the like; and are modified or bound to a liposome in a preferable embodiment. When the vector is a liposome, the GALA peptide may be bound to any of the components of the liposome, such as a phospholipid, cholesterol, a lipid (preferably a cationic lipid), and a helper lipid. The GALA peptide of SEQ ID NO: 1 bound to cholesterol (cholesteryl-OH) has, for example, the following structure (hereinafter, sometimes abbreviated as "Chol-GALA"):

In the description above, "—O(C=O)—" is bound to the amino group at the N-terminal of the GALA peptide, and "—NH$_2$" means that the carboxyl group at the C-terminal of the GALA peptide is protected with an amino group. The bond formed between cholesterol and the GALA peptide may be a urethane bond as shown above, or may be an ester bond or an ether bond. The cholesteryl group may be bound to the GALA peptide at either the N-terminal or the C-terminal, or may be bound to a side chain of any amino acid of the GALA peptide. Furthermore, the cholesteryl group may be bound to the GALA peptide via any linker such as an alkylene, a peptide, or a polyether. Furthermore, although the C-terminal is an amide in the description above, the C-terminal may be other groups such as carboxylic acid (COOH), ester, or a salt of carboxylic acid.

When the GALA peptide is bound to a lipid component such as cholesterol and phospholipid, and is included in a vector or a substance introduction agent; the amount of the included GALA peptide with respect to the total lipid amount is about 0.1 to 5 mol %, preferably 0.3 to 4 mol %, more preferably 0.5 to 4 mol %, further preferably 1 to 4 mol %, particularly preferably 1.5 to 2 mol %. It should be noted that, the "total lipid amount" described in the present specification does not include the amount of lipid components bound to a modification component of a liposome. That is, the amount of a lipid component bound to the GALA peptide is not included. Similarly, when the vector is modified with PEG, the amount of lipid component bound to PEG is not included.

For example, when the lipid components (total lipid amount) not bound to the GALA peptide is 100 mol and the lipid components bound to the GALA peptide is 5 mol, a GALA modification level (a ratio of lipid bound to the GALA peptide with respect to the total lipid amount) is 5 mol %.

When the vector is formed from components other than lipids, the amount of the GALA peptide with respect to the total weight of the vector is about 0.01 to 10 wt %, preferably 0.1 to 5 wt %, more preferably 0.5 to 4 wt %, and particularly preferably 1 to 2.5 wt %.

Although an embodiment in which the GALA peptide is bound to cholesterol is described above, the GALA peptide may be bound to components of the vector other than cholesterol, and modes thereof are obvious to those skilled in the art.

Zeta-potential of the vector and the substance introduction agent of the present invention is, at a pH near neutral (e.g., pH 7 or 7.4), about −100 to 100 mV, preferably about −50 to 50 mV, and more preferably about −30 to 30 mV. The zeta-potential can be measured using a zetasizer.

The mean particle diameters of the vector and the substance introduction agent of the present invention are not particularly limited, and, for example, the particle diameter is 30 to 1000 nm, preferably 50 to 300 nm, more preferably 50 to 200 nm, and particularly preferably 50 to 150 nm. The mean particle diameter can be measured by, for example, dynamic light scattering method, static light scattering method, electron microscopy, atomic force microscopy, etc.

The introduction agent of the present invention includes the vector together with an intended substance that is to be delivered within a cell. The intended substance may have a covalent bond formed with the vector, may form a complex with the vector, and, when the vector is a hollow particle, may be enclosed or encapsulated inside the vector. The intended substance of the present invention is particularly a bioactive substance that takes effect when introduced into pulmonary cells.

The substance introduction agent of the present invention may be used both in vitro and in vivo for delivering the intended substance in pulmonary cells.

The type of the intended substance is not particularly limited, and examples thereof include: drugs, nucleic acids, peptides (peptide hormones, bioactive peptides, etc., such as oxytocin, bradykinin, thyrotropin releasing factor, and enkephalin), proteins (enzymes, various cytokines such as interleukin, cell transfer factor, cell growth factor, etc.), sugars, or complexes of those. The type of the intended substance may be appropriately selected depending on the purpose of treatment, diagnosis, the type of pulmonary disease, etc. It should be noted that "nucleic acid" includes, in addition to DNA or RNA, an analog or a derivative thereof (e.g., siRNA, peptide nucleic acid (PNA), phosphorothioate DNA, etc.). Furthermore, the nucleic acid may be either single-stranded or double-stranded, and may be either linear or circular.

When the intended substance is a drug, examples thereof include anticancer agents, vasodilator drugs, pulmonary vasculitis therapeutic agents, antibacterial agents antivirus agents, anti-inflammatory agents, bronchodilators, antitussive agents, pulmonary fibrosis inhibitors, antituberculous drugs, and the like. Specific examples of anticancer agents include doxorubicin, daunorubicin, cisplatin, oxaliplatin, carboplatin, paclitaxel, irinotecan, SN-38, actinomycin D, vincristine, vinblastine, methotrexate, azathioprine, fluorouracil, mitomycin C, docetaxel, cyclophosphamide, capecitabine, epirubicin, gemcitabine, mitoxantrone, leucovorin, vinorelbine, trastuzumab, etoposide, estramustine, prednisone, interferon-alpha, interleukin-2, bleomycin, ifosfamide, mesna, altretamine, topotecan, cytarabine, methylprednisolone, dexamethasone, mercaptopurine, thioguanine, fludarabine, gemtuzumab, idarubicin, mitoxantrone, tretinoin, alemtuzumab, chlorambucil, cladribine, imatinib, epirubicin, dacarbazine, procarbazine, mechlorethamine, rituximab, denileukin diftitox, trimethoprim/sulfamethoxazole, allopurinol, carmustine, tamoxifen, filgrastim, temozolomide, melphalan, vinorelbine, azacytidine, thalidomide, mitomycin, and the like. Specific examples of vasodilator drugs include bosentan, ambrisentan, beraprost sodium, sildenafil, epoprostenol, and the like. Specific examples of pulmonary vasculitis therapeutic agents include adrenal cortical steroid, cyclophosphamide, azathioprine, methotrexate, aspirin, and the like. Specific examples of antibacterial agents include amphotericin B and the like. Specific examples of antivirus agents include vidarabine, acyclovir, trifluoro thymidine, and the like. Specific examples of anti-inflammatory agents include phenylbutazone, acetaminophen, ibuprofen, indomethacin, sulindac, piroxicam, diclofenac, prednisone, beclomethasone, dexamethasone, and the like.

When the intended substance is a nucleic acid, preferable examples thereof include a double-stranded RNA (dsRNA) selected from the group consisting of meroduplex RNA (mdRNA), nicked dsRNA (ndsRNA), gapped dsRNA (gdsRNA), short interfering nucleic acid (siNA), siRNA, micro RNA (miRNA), short hairpin RNA (shRNA), short interfering oligonucleotide, substituted short interfering oligonucleotide, modified short interfering oligonucleotide, chemically modified dsRNA, and post transcriptional gene silencing RNA (ptgsRNA). The intended substance may be used alone, or a mixture of two or more types of the intended substance may be used. For example, it is possible to use a combination of two or more types of siRNAs. When the substance introduction agent includes a nucleic acid such as siRNA as the intended substance, a cation such as polyethyleneimine (PEI) is preferably also included together.

In one embodiment with a substitution and modification (including chemical modification), double-stranded RNA may include an overhang containing a deoxyribonucleotide or two deoxyribonucleotides (e.g., thymidine, adenine), or an overhang of 1 to 4 nucleotides at one or both of the 3' ends of the double-stranded RNA. The double-stranded RNA may include a blunt end at one or both ends. In some of the embodiments, 5' ends of the first and second strands are phosphorylated. In all embodiments with a double-stranded RNA, a nucleotide overhang at the 3' end may include a deoxyribonucleotide or ribonucleotide having a chemical modification at the backbone, base, or sugar of the nucleic acid. In all embodiments with a double-stranded RNA, a nucleotide overhang at the 3' end may include one or more universal base ribonucleotide. In all embodiments with a double-stranded RNA, a nucleotide overhang at the 3' end may include one or more acyclic nucleotide. In all embodiments with a double-stranded RNA, the dsRNA may further include a terminal phosphate group such as 5',3'-diphosphate or 5'-phosphate (cf. Martinez et al., Cell. 110:563-574, 2002; and Schwarz et al., Molec. Cell. 10:537-568, 2002).

The double-stranded RNA may further include a 2'-sugar substitution such as 2'-deoxy, 2'-O-methyl, 2'-O-methoxy ethyl, 2'-O-2-methoxy ethyl, halogen, and 2'-fluoro, 2'-O-allyl, or any combination thereof. In additional embodiments, the double-stranded RNA may further include a terminal cap substituent such as alkyl, abasic, deoxy abasic, glyceryl, dinucleotide, acyclic nucleotide, inverted deoxynucleotide moiety, or any combination thereof, at one end or both ends of the first strand or one or more of the second strand.

Furthermore, in another embodiment, the double-stranded RNA may include at least one modified inter-nucleotide bond such as phosphorothioate, chiral phosphorothioate, phosphorodithioate, phosphotriester, amino alkyl phosphotriester, methyl phosphonate, alkyl phosphonate, 3'-alkylene phosphonate, 5'-alkylene phosphonate, chiral phosphonate, phosphonoacetate, thiophosphonoacetate, phosphinate, phosphoramidate, 3'-amino phosphoramidate, amino alkyl phosphoramidate, thionophosphoramidate, thionoalkylphosphonate, thionoalkylphosphotriester, selenophosphate, or boranophosphate bond, independently or any combination thereof.

The double-stranded RNA may be substituted or modified (including chemical modification) by using a nucleic acid analog including: 5-methyl cytosine; 5-hydroxymethylcytosine; xanthine; hypoxanthine; 2-amino adenine; 6-methyl; 2-propyl or other alkyl derivatives such as adenine and guanine; 8-substituted adenine and guanine (8-aza-, 8-halo, 8-amino, 8-thiol, 8-thioalkyl, 8-hydroxyl, etc.); 7-methyl, 7-deaza, and 3-deazaadenine, and guanine; 2-thiouracil; 2-thiothymine; 2-thiocytosine; 5-methyl, 5-propynyl, 5-halo (5-bromo, 5-fluoro, or the like), 5-trifluoromethyl, or other 5-substituted uracil and cytosine; and 6-azo uracil.

RNA such as double-stranded RNA (dsRNA) may be chemically modified. Non-restrictive examples of such chemical modification include introduction of phosphorothioate bond between nucleotides, 2'-deoxyribonucleotide, 2'-O-methyl ribonucleotide, 2'-deoxy-2'-fluoro ribonucleotide, "acyclic" nucleotide, 5'-C-methyl nucleotide, and glyceryl and/or an inverted deoxy abasic residue to the end. These chemical modifications can maintain RNAi activity within a cell.

As long as the liposome is a closed vesicle having a lipid bilayer structure, the liposome may be a multilamellar liposome (MLV), or a unilamellar liposome such as a SUV (small unilamellar vesicle), a LUV (large unilamellar vesicle), and a GUV (giant unilamellar vesicle).

The vector (carrier) of the present invention may be modified with a hydrophilic polymer.

Examples of the hydrophilic polymer include polyalkylene glycols (polyethylene glycol, polypropylene glycol, polybutylene glycol, or a copolymer of polyalkylene glycols such as a block copolymer of polyethylene glycol and polypropylene glycol), dextran, pullulan, ficoll, polyvinyl alcohol, styrene-maleic anhydride alternating copolymers, divinyl ether-maleic anhydride alternating copolymers, amylose, amylopectin, chitosan, mannan, cyclodextrin, pectin, carrageenan, and the like. The hydrophilic polymer is preferably a polyalkylene glycol (polyethylene glycol, polypropylene glycol, polybutylene glycol, or a copolymer of polyalkylene glycols such as a block copolymer of polyethylene glycol and polypropylene glycol), and is particularly preferably polyethylene glycol (PEG); and the vector (carrier) is preferably modified with these hydrophilic polymers. The length of the PEG may be appropriately selected from a range of molecular weight of about 500 to 10000, and a preferable molecular weight is 1000 to 5000, and a more preferable molecular weight is 2000. Examples of the lipid modified with PEG include DSPE (distearoyl phosphatidylethanolamine)-PEG2000, DMPE (dimyristoyl phosphatidylethanolamine)-PEG2000, DSG (distearoyl glycerol)-PEG2000, DMG (dimyristoyl glycerol)-PEG2000, cholesterylated PEG2000, STR (Stearyl)-PEG2000 or C8 ceramide-PEG2000, C16 ceramide-PEG2000, and the like. Among these, STR-PEG2000 or C8 ceramide-PEG2000 is preferable. The molecular weight of other hydrophilic polymers may be appropriately selected similarly by those skilled in the art.

For example, when a liposome is to be PEG-modified, usage of stearylated PEG (STR-PEG), C8 ceramide-PEG, or cholesterylated PEG (Chol-PEG) is preferable for obtaining a vector (e.g., liposomal formulation) having excellent storage stability without impairing the lung migratability and the functional expression of the intended substance (e.g., nucleic acid medicine such as siRNA). Furthermore, usage of DSPE-PEG, DSG-PEG, C16 ceramide-PEG, or the like is preferable for improving in-blood stability.

When the hydrophilic polymer is to be used for modifying a liposome, the hydrophilic polymer is preferably used for modification at a ratio of about 1 to 15 mol % when lipids forming the liposome is 100 mol %.

In the following, although the vector (carrier) for delivering an intended substance to a lung in vitro or in vivo will be described by using a liposome as an example, the present invention is not limited to a liposome, and any vector (carrier) capable of introducing the GALA peptide into a cell is included in the present invention.

In the liposome of the present invention, the type of lipid forming a lipid bilayer is not particularly limited, and specific examples thereof include: phospholipids such as phosphatidylcholines (e.g., dioleoyl phosphatidylcholine, dilauroyl phosphatidylcholine, dimyristoyl phosphatidylcholine, dipalmitoyl phosphatidylcholine, distearoyl phosphatidylcholine, and the like), phosphatidylglycerols (e.g., dioleoyl phosphatidylglycerol, dilauroyl phosphatidylglycerol, dimyristoyl phosphatidylglycerol, dipalmitoyl phosphatidylglycerol, and distearoyl phosphatidylglycerol), phosphatidylethanolamines (e.g., dioleoyl phosphatidylethanolamine, dilauroyl phosphatidylethanolamine, dimyristoyl phosphatidylethanolamine, dipalmitoyl phosphatidylethanolamine, and distearoyl phosphatidylethanolamine), phosphatidylserines, phosphatidylinositols, phosphatidic acid, cardiolipin, and the like; hydrogenated products thereof; and glycolipids such as sphingomyelin and ganglioside. With regard to the lipids, a single lipid may be used alone, or a combination of two or more lipids may be used. The phospholipid may be a natural lipid derived from egg yolk, soybean, or other lipids from animals and plants (e.g., egg yolk lecithin, soybean lecithin, and the like); a synthetic lipid; or a semi-synthetic lipid. With regard to the lipids, a single lipid may be used alone, or a combination of two or more lipids may be used.

For the purpose of physically or chemically stabilizing the lipid bilayer, or adjusting fluidity of the membrane, the lipid bilayer may include one or more of, for example: animal derived sterols such as cholesterol, cholesterol succinate, lanosterol, dihydrolanosterol, desmosterol, and dihydrocholesterol; plant derived sterols (phytosterol) such as stigmasterol, sitosterol, campesterol, and brassicasterol; microbe derived sterols such as zymosterol and ergosterol; sugars such as glycerol and sucrose; and glycerin fatty acid esters such as triolein and trioctanoin. Although the contained amount of those is not particularly limited, the contained amount with respect to the total amount of lipid forming the lipid bilayer is preferably 5 to 40% (molar ratio), and further preferably 10 to 30% (molar ratio).

The lipid bilayer may include: antioxidants such as tocopherol, propyl gallate, ascorbyl palmitate, and butylated hydroxytoluene; charged substances that give a positive charge such as stearylamine and oleyl amine; charged substances that give a negative charge such as dicetyl phosphate; and membrane proteins such as membrane surface proteins and membrane intrinsic proteins. The contained amount of those may be appropriately controlled.

The liposome of the present invention has, on the surface thereof, a GALA peptide formed from 30 amino acids. It should be noted that, the surface of the liposome in a unilamellar liposome is the outer surface of a lipid bilayer, and the surface of the liposome in a multilamellar liposome is the outer surface of a lipid bilayer at the outermost layer. Furthermore, the liposome of the present invention may also include the peptide at a part (e.g., inner surface of the lipid bilayer) other than the surface.

The vector of the present invention preferably includes a cationic lipid. Examples of the cationic lipid include DODAC (dioctadecyldimethylammonium chloride), DOTMA (N-(2,3-dioleyloxy)propyl-N,N,N-trimethylammonium), DDAB (didodecylammonium bromide), DOTAP (1,2-dioleoyloxy-3-trimethylammonio propane), DC-Chol (3-beta-N—(N',N',-dimethyl-aminoethane)-carbamol cholesterol), DMRIE (1,2-dimyristoyloxypropyl-3-dimethylhydroxyethyl ammonium), DOSPA (2,3-dioleyloxy-N-[2(sperminecarboxamido)ethyl]-N,N-dimethyl-1-propanaminum trifluoroacetate), DSTAP (1,2-Distearoyl-3-Trimethylammonium Propane), DODAP (dioleoyl-3-dimethylammonium-propane), and the like. The cationic lipid is preferably DOTMA, DSTAP, or DODAP, and is particularly preferably DOTMA. With regard to the cationic lipid, a single cationic lipid may be used alone, or a combination of two or more cationic lipids may be used.

Of the cationic lipids, DOTMA and DSTAP have a quaternary amine and consistently have a positive charge, whereas DODAP has a tertiary amine and does not have a charge in a physiological pH. Therefore, by changing the type and blended amount of the cationic lipids, it is possible to provide a breadth to the structure and characteristics of the cationic lipid.

The vector of the present invention preferably includes a helper lipid. Examples of the helper lipid include EPC (egg phosphatidylcholine), DLPC (dilinoleoylphosphatidylcholine), DMPC (dimyristoylphosphatidylcholine), DPPC (dipalmitoylphosphatidylcholine), DSPC (distearoylphosphatidylcholine), POPC (palmitoyloleoylphosphatidylcholine), DOPC (dioleoylphosphatidylcholine), DOPE (dioleoyl-phosphatidylethanolamine), and SOPE (stearyloleoylphosphatidylcholine). Among these, EPC, DOPC, DOPE, and SOPE are preferable.

For example, since a MEND including DOPC as a helper lipid does not aggregate at all after being stored at room temperature for 1 month, DOPC is excellent also in terms of storage stability.

As a preferable mode of the liposome of the present invention, a liposome can be illustrated in which the GALA peptide is modified with a hydrophobic group or a hydrophobic compound, and the hydrophobic group or the hydrophobic compound is inserted in a lipid bilayer whereas the peptide is exposed from the lipid bilayer. It should be noted that, in the present mode, "the peptide is exposed from the lipid bilayer" includes a case where the peptide is exposed from either the outer surface or inner surface of the lipid bilayer, and a case where the peptide is exposed from both surfaces.

The hydrophobic group or hydrophobic compound is not particularly limited as long as it can be inserted in a lipid bilayer. Examples of the hydrophobic group include: saturated or unsaturated fatty acid groups such as stearyl group, palmityl group, oleyl group, palmitoleyl group, linolyl group, linoleyl group, and the like, aliphatic alcohols, aliphatic amines, or other groups (e.g., sterol derived groups such as cholesteryl group (Chol)) including hydrocarbon groups whose carbon number is 10 or larger; and derivatives thereof. Among these, fatty acid groups whose carbon number is 10 to 20 (e.g., palmitoyl group, oleyl group, stearyl group, arachidonoyl group, and the like) are particularly preferable. In addition, examples of the hydrophobic compound include the above illustrated phospholipids, glycolipids, or sterols, long-chain aliphatic alcohols (e.g., phosphatidylethanolamine, cholesterol, and the like), polyoxypropylene alkyl, glycerin fatty acid esters, and the like.

The liposome of the present invention may be created using a method known in the art, including, for example, hydration method, ultrasonication, ethanol injection method, ether injection method, reversed phase evaporating method, and freezing-and-thawing method.

A method for producing the liposome using the hydration method will be shown below.

A lipid, which is a component of a lipid bilayer, and the peptide modified with the hydrophobic group or the hydrophobic compound is dissolved in an organic solvent, and then the organic solvent is removed through evaporation to obtain a lipid membrane. In this case, examples of the organic solvent include: hydrocarbons such as pentane, hexane, heptane, and cyclohexane; halogenated hydrocarbons such as methylene chloride and chloroform; aromatic hydrocarbons such as benzene and toluene; lower alcohols such as methanol and ethanol; esters such as methyl acetate and ethyl acetate; and ketones such as acetone. With regard to these organic solvents, a single organic solvent may be used alone, or a combination of two or more organic solvents may be used. Next, by hydrating the lipid membrane and stirring or ultrasonicating the solution, a liposome having the peptide on the surface thereof can be produced.

Furthermore, another production example using the hydration method will be shown in the following.

A lipid, which is a component of a lipid bilayer, is dissolved in an organic solvent, and then the organic solvent is removed through evaporation to obtain a lipid membrane. The lipid membrane is hydrated, and the solution is stirred or ultrasonicated to produce a liposome. Next, by adding the peptide modified with the hydrophobic group or the hydrophobic compound to the external solution of the liposome, the peptide can be introduced to the surface of the liposome. Alternatively, by adding the peptide modified with the hydrophobic group or the hydrophobic compound to the organic solvent having dissolved therein the lipid, the peptide can be introduced to the surface of the liposome.

For example, when a quaternary amine is used as the cationic lipid, the liposome can be produced using a method similar to that in Example 3-1 described later, a method based thereon, or a combination of those and a method commonly used in the art; and when a tertiary amine is used as the cationic lipid, the liposome can be produced using a method similar to that in Example 3-2 described later, a method based thereon, or a combination of those and a method commonly used in the art.

When preparing the cationic liposome, the ratio of cationic lipid/Chol/helper lipid can be changed as appropriate. The composition ratio (molar ratio) is preferably 10 to 50/20 to 50/20 to 70, more preferably 20 to 40/30 to 50/20 to 40, and particularly preferably 30/40/30. A preferable combination of cationic lipid/Chol/helper lipid is a cationic lipid selected from DOTMA, DODAP, or DSTAP/Chol/a helper lipid selected from EPC, DOPE, or SOPE, and is more preferably DOTMA/Chol/EPC, DODAP/Chol/EPC, DSTAP/Chol/EPC, DOTMA/Chol/DOPE, or DOTMA/Chol/SOPE. When the liposome is to be modified with Chol-GALA, the added ratio of Chol-GALA can be changed as appropriate, and examples thereof with respect to the total lipid amount (total amount of lipid of cationic lipid/Chol/helper lipid) include 0.1 to 5 mol %, preferably 0.3 to 4 mol %, more preferably 0.5 to 4 mol %, further preferably 1 to 4 mol %, and particularly preferably 1.5 to 2 mol %. In addition, the liposome may be modified with PEG as appropriate, and when conducting the PEG modification, the added ratio of PEG can be changed as appropriate, and examples of the added ratio with respect to the total lipid amount (total amount of lipid of cationic lipid/Chol/helper lipid) include 0.1 to 15 mol %, and is preferably 1 to 5 mol %. It should be noted that the added PEG is preferably a PEG bound to lipid, more preferably STR-PEG or C8 ceramide-PEG, and particularly preferably STR-PEG2000 or C8 ceramide-PEG2000.

In addition, by using the above described helper lipid, a neutral liposome whose liposome composition is helper lipid/Chol can be prepared, and although the composition ratio (molar ratio) thereof can be changed as appropriate, the composition ratio is preferably 40 to 90/10 to 60, more preferably 60 to 80/20 to 40, and particularly preferably 70/30. The combination of helper lipid/Chol is preferably EPC/Chol, DLPC/Chol, DMPC/Chol, DPPC/Chol, DSPC/Chol, POPC/Chol, DOPC/Chol, DOPE/Chol, or SOPE/Chol, more preferably EPC/Chol, DOPC/Chol, DOPE/Chol, or SOPE/Chol, and particularly preferably EPC/Chol. When the liposome is to be modified with Chol-GALA, the added ratio of Chol-GALA can be changed as appropriate, and examples thereof with respect to the total lipid amount (total amount of lipid of helper lipid/Chol) include 0.1 to 5 mol %, preferably 0.3 to 4 mol %, more preferably 0.5 to 4 mol %, further preferably 1 to 4 mol %, and particularly preferably 1.5 to 2 mol %. In addition, the liposome may be modified with PEG as appropriate, and when conducting the PEG modification, the added ratio of PEG can be changed as appropriate and examples of the added ratio with respect to the total lipid amount (total amount of lipid of helper lipid/Chol) include 0.1 to 15 mol %, and is preferably 1 to mol %. It should be noted that the added PEG is preferably a PEG modified onto lipid, more preferably STR-PEG or C8 ceramide-PEG, and particularly preferably STR-PEG2000 or C8 ceramide-PEG2000.

The liposome composition of the present invention is preferably cationic lipid/Chol/helper lipid/STR-PEG/Chol-GALA or helper lipid/Chol/STR-PEG/Chol-GALA, more preferably a cationic lipid selected from DOTMA, DODAP, or DSTAP/Chol/a helper lipid selected from EPC, DOPE, or SOPE/STR-PEG/Chol-GALA, or EPC/Chol/STR-PEG/Chol-GALA, and further preferably DOTMA/Chol/EPC/STR-PEG/Chol-GALA, DODAP/Chol/EPC/STR-PEG/Chol-GALA, DSTAP/Chol/EPC/STR-PEG/Chol-GALA, DOTMA/Chol/DOPE/STR-PEG/Chol-GALA, DOTMA/Chol/SOPE/STR-PEG/Chol-GALA, or EPC/Chol/STR-PEG/Chol-GALA. It should be noted that, as STR-PEG, STR-PEG2000 whose PEG has a molecular weight of 2000 is particularly preferable.

The most preferable liposome of the present invention has a composition of DOTMA/Chol/EPC/STR-PEG2000/Chol-GALA, wherein:

preferably, the composition ratio (molar ratio) of DOTMA/Chol/EPC therein is 10 to 50/20 to 50/20 to 70, and, with respect to the total lipid amount of DOTMA/Chol/EPC, STR-PEG2000 is included by 1 to 15 mol % and Chol-GALA is included by 0.1 to 5 mol %;

more preferably, the composition ratio (molar ratio) of DOTMA/Chol/EPC therein is 20 to 40/30 to 50/20 to 40, and, with respect to the total lipid amount of DOTMA/Chol/EPC, STR-PEG2000 is included by 1 to 5 mol % and Chol-GALA is included by 1 to 4 mol %; and most preferably, the composition ratio (molar ratio) of DOTMA/Chol/EPC therein is 30/40/30, and, with respect to the total lipid amount of DOTMA/Chol/EPC, STR-PEG2000 is included by 1 to 5 mol % and Chol-GALA is included by 1.5 to 2 mol %. Since STR-PEG2000 and Chol-GALA are modification components of the liposome, added amounts of those are represented as a ratio with respect to 100 mol %, i.e., the total lipid amount of liposome formed from three components of DOTMA/Chol/EPC.

The intended substance that is to be delivered to pulmonary cells can be encapsulated inside the liposome of the present invention.

Examples of the intended substance encapsulated in the substance introduction agent (in particular, liposome) of the present invention include, depending on the type of pulmonary disease, the drugs described above (anticancer agents, vasodilator drugs, antibacterial agents, and the like), nucleic acids (DNA, RNA, and analogs or derivatives thereof (e.g., siRNA, peptide nucleic acid (PNA), phosphorothioate DNA, etc.), and peptides (peptide hormones and bioactive peptides such as oxytocin, bradykinin, thyrotropin releasing factor, and enkephalin). Treatment or prevention of a pulmonary disease is possible by encapsulating a suitable intended substance depending on the type of the pulmonary disease. In the present specification, "pulmonary disease" includes, but not limited to lung cancer, inflammatory diseases of the lung, pulmonary fibrosis, pulmonary embolism, pulmonary hypertension, pulmonary vasculitis, acute respiratory distress syndrome (ARDS), asbestosis/dust disease, asthma, bronchiectasis, bronchopulmonary dysplasia (BPD), chronic bronchitis, chronic cough, chronic obstructive pulmonary disease (COPD), common cold, cystic fibrosis, emphysema, hantavirus, histoplasmosis, influenza, Legionnaires' disease, lymphangioleiomyomatosis, pertussis, pleurisy, pneumothorax, primary alveolar hypoventilation syndrome, pulmonary alveolar proteinosis, respiratory distress syndrome, RS virus, sarcoidosis, severe acute respiratory syndrome (SARS), tuberculosis, or the like. A pulmonary disease that is preferable as the target for treatment or prevention is a pulmonary disease involved in blood vessels of the lung, and examples thereof include lung cancer, pulmonary hypertension, pulmonary vasculitis, and the like; and lung cancer (including non-small cell lung cancer, small cell lung cancer) is particularly preferable. The lung cancer not only includes primary lung cancer, but also includes metastatic lung cancer metastasized from organs other than the lung. Furthermore, the substance introduction agent of the present invention can also be used for suppressing metastasis of cancer, which is a cancer whose primary focus is the lung, to other organs (e.g., adrenal gland, liver, brain, bones, or the like). The intended substance that is to be encapsulated in the substance introduction agent of the present invention for treating lung cancer and for suppressing metastasis of cancer from the lung is: preferably an anticancer agent described above (e.g., amrubicin hydrochloride, gefitinib, cisplatin, vinblastine, mitomycin C, vinorelbine, paclitaxel, docetaxel, gemcitabine, carboplatin, irinotecan, tegafur, etoposide, vincristine, cyclophosphamide, doxorubicin, ifosfamide, vindesine, and the like) or an siRNA whose target is a factor involved in angiogenesis (e.g., CD31, ESAM, VEGF, VEGFR, EGF, EGFR, D11, SFRP, CD151, bFGF, TGF beta 1, PDGF, HGF, and the like); more preferably an siRNA whose target is CD31, ESAM, CD151, VEGF, or EGF; and particularly preferably an anti-CD31 siRNA. Depending on the purpose, these agents may be used singly or as a mixture of two or more.

The intended substance encapsulated in the substance introduction agent of the present invention for pulmonary hypertension is preferably a vasodilator described above (e.g., bosentan, ambrisentan, beraprost sodium, sildenafil, epoprostenol, and the like) or an anti siRNA of a factor involved in vasodilatation (e.g., endothelin receptor ($ET_A$, $ET_B$), PDE5, and the like).

The intended substance encapsulated in the substance introduction agent of the present invention for pulmonary vasculitis is preferably adrenal cortical steroid, cyclophosphamide, azathioprine, methotrexate, aspirin, and the like.

The substance introduction agent of the present invention may be used singly or may be used together with other treatments for pulmonary diseases.

When the intended substance is water soluble, the intended substance can be encapsulated in an aqueous phase inside the liposome by adding the intended substance to an aqueous solvent used when hydrating the lipid membrane for producing the liposome. When the intended substance is lipophilic, the intended substance can be encapsulated in the lipid bilayer of the liposome by adding the intended substance to an organic solvent used for producing the liposome. In the present specification, "encapsulate" includes both a case in which of the intended substance is included inside a hollow particle such as a liposome and a case in which the intended substance is retained at the surface portion forming the vector, such as a lipid bilayer membrane.

The biological species to which the intended substance is to be delivered is not particularly limited as long as the species is a vertebrate having a lung, and is preferably a mammal. Examples of such mammal include human, monkey, cow, sheep, goat, horse, pig, rabbit, dog, cat, rat, mouse, guinea pig, and the like.

The liposome of the present invention may be used, for example, in a state of a dispersion liquid. As a dispersing solvent, for example, a buffer such as acetate buffer, citrate buffer, phosphate buffer, or saline solution can be used. To the dispersion liquid, for example, additives such as sugars, polyhydric alcohols, water soluble polymers, nonionic surfactants, antioxidants, pH modifiers, hydration promoters, etc., may be added.

The liposome of the present invention may be used in a form obtained by drying the dispersion liquid (e.g., lyophilization, spray drying, and the like). A dried liposome may be added to a buffer such as acetate buffer, citrate buffer, phosphate buffer, or saline solution to obtain a dispersion liquid.

Each of the liposomes can be used both in vitro and in vivo. When each of the liposomes is used in vivo, examples of the administration route include intravenous injection, intravenous dripping, and the like; and the administration dose and administration frequency may be appropriately adjusted depending on the amount and type etc., of the intended substance encapsulated in the liposome according to the present invention.

The liposome of the present invention has not shown to cause weight reduction or liver damage, and can be safely administered.

EXAMPLES

In the following, although the present invention will be described in more detail based on Examples, it is needless to say that the present invention is not limited the Examples.

The reagents, material, animals, etc., used in each of the Examples are shown in the following.

EPC was purchased from NOF Corp., (Tokyo, JAPAN). DOTAP, DSTAP, DODAP, cholesterol, DOPE, SOPE, DOPC, and C8-ceramide-PEG2000 were purchased from Avanti Polar Lipids (Alabaster, Ala., USA). DOTMA was purchased from Tokyo Chemical Industry Co., Ltd. (Tokyo, JAPAN). STR-PEG2000 was purchased from Wako Pure Chemical Industries, Ltd.

Chol-GALA (cholesteryl-O(C=O)-WEAALAEALAEA-LAEHLAEALAEALEALAA-$NH_2$; Mw. 3444.0; >71% purity) was synthesized using a method described in Patent Literature 3, a method based thereon, or a combination of those and a method commonly used in the art.

PEI (branch type, Mw. ave.10,000) was purchased from Wako Pure Chemical Industries, Ltd.

Transaminase CII-Test Wako was purchased from Wako Pure Chemical Industries, Ltd.

RNAlater was purchased from Ambion. High Capacity RNA-to-cDNA Kit and TaqMan Gene Expression Master Mix were purchased from Applied Biosystems. Synthesis of siRNA and Cy5 labeled siRNA were contracted out to Hokkaido System Science Co. Ltd. Synthesis of primers and probes were conducted in accordance with a method commonly used in the art. Sequences of the used siRNA, primers, and probes are shown in the following.

siRNA

```
CD31-1 sense:
GCACAGUGAUGCUGAACAAUU      (SEQ ID NO: 2)

CD31-1 antisense:
UUGUUCAGCAUCACUGUGCUU      (SEQ ID NO: 3)

CD31-2 sense:
GUGCAUAGUUCAAGUGACAUU      (SEQ ID NO: 4)

CD31-2 antisense:
UGUCACUUGAACUAUGCACUU      (SEQ ID NO: 5)

CD31-3 sense:
GCAAGAAGCAGGAAGGACAUU      (SEQ ID NO: 6)

CD31-3 antisense:
UGUCCUUCCUGCUUCUUGCUU      (SEQ ID NO: 7)

Luciferase sense:
GCGCUGCUGGUGCCAACCUU       (SEQ ID NO: 8)

Luciferase antisense:
GGGUUGGCACCAGCAGCGCUU      (SEQ ID NO: 9)
```

As the CD31 siRNA, the above described 3 types were mixed in equal amount to be used.

Primer, Probe

```
CD31 Forward:
                           (SEQ ID NO: 10)
CAGAGCGGATAATTGCCATTCC CD31 Reverse:
                           (SEQ ID NO: 11)
ACAGGATGGAAATCACAACTTCATC CD31 Probe:
                           (SEQ ID NO: 12)
[FAM] ACCCTCAGGATCTCGCTGAACACCGC [TAMRA]

CD34 Forward:
                           (SEQ ID NO: 13)
TCTGCCTGGAACTAAGTGAAGC

CD34 Reverse:
                           (SEQ ID NO: 14)
CCTCAGACTGGGCTAGAAGCA

CD34 Probe:
                           (SEQ ID NO: 15)
[FAM] ACCAGCATCAGCCTCAGCCTCCTCC [TAMRA]
```

ICR male mice of 5 weeks of age and C57BL/6 male mice that were 6 weeks of age were purchased from Japan SLC, Inc.

For others, unless mentioned otherwise, a special grade or first grade commercially available product, or one that is similar to that was used.

In addition, instruments and the like used in each of the Examples are shown in the following.

For the preparation of a lipid membrane, a pump DIVAC 1.2 and a trap EVALA UNI TRAP UT-1000 were used (both from Tokyo Rikakikai Co., Ltd.).

A bathtub type sonicator AU-25C (AIWA MEDICAL INDUSTRY Co., Ltd.) was used for ultrasonication. ZETA SIZER Nano-ZS (Malvern Instruments Ltd.) was used for measuring zeta potential and particle diameter with dynamic light scattering (DLS).

ABI 7500 real-time system (Applied Biosystems) was used for real-time PCR.

A liquid scintillation counter TRI-CABB 1600TR (PACKARD) was used to measure beta ray.

As a confocal laser scanning microscope (CLSM), A1 (Nikon), objective lens Plan Apo VC 20× and 60×, and lasers of Ar laser and He/Ne laser were used.

PCR thermal cycler TP3000 (Takara Bio, Inc.) was used for reverse transcription.

Docu-pH Meter (Sartorius) was used for measuring pH.

The used lipid was prepared in a desired concentration (1 to 10 mM) through dilution with a proper amount of EtOH.

Chol-GALA was purified with reversed-phase HPLC using COSMOSIL 5C4-AR-300 (size: 10×250 mm). $H_2O$/0.1% TFA was used as buffer A, and $CH_3CN$/0.1% TFA was used as buffer B. Chol-GALA (purity: >71%) dissolved in DMF was injected (4 mg/mL as Crude), and a gradient was applied at flow rate of 2.0 mL/min, 25° C., and 50% B=>95% B (20 min) (the details are described below). Chol-GALA was collected by detecting absorbance at 215 nm, and was lyophilized. The purity of the purified Chol-GALA was examined using HPLC, and then the purified Chol-GALA was dispensed as a 1 mM EtOH solution and stored at −80° C.

<Conditions>

Injection amount: 250 μL (4 mg/mL in DMF)

Flow rate: 2 mL/min

Column temperature: 25° C.:

Protocol:

TABLE 1

| Time (min) | Buffer B (%) |
|---|---|
| 0 | 50 |
| 20 | 95 |
| 40 | 95 |
| 40.5 | 100 |
| 45.5 | 100 |
| 46 | 50 |
| 60 | 50 |

Particle diameter and zeta-potential of the liposome and MEND were measured using Zetasizer Nano ZS (Malvern Instruments, UK).

Unless mentioned otherwise, experimental data was described as average value plus-and-minus standard deviation of three or more experimental values. For testing significance, one-way ANOVA test was conducted, and multiple comparison was conducted with Dunnett method, and a value with $P<0.05$ was regarded as significant.

Example 1

Liposome Preparation

1) Lipid Membrane Preparation

In a glass test tube, EPC (EtOH solution) and Chol (EtOH solution) were prepared in a molar ratio of 70/30 (liposome a), STR-PEG2000 (EtOH solution) was added thereto so as to be 5 mol % with respect to the total lipid amount of liposome a, a suitable amount of EtOH was added thereto, and then the test tube was dried under reduced pressure in a desiccator to distill off solvents to prepare a lipid membrane whose lipid composition was EPC/Chol/STR-PEG2000 (abbreviated as "Liposome" in FIG. 1). Furthermore, when modifying EPC/Chol/STR-PEG2000 with Chol-GALA, 2 mol % thereof with respect to the total lipid amount of liposome a was added in the lipid solution to prepare a lipid membrane whose lipid composition was EPC/Chol/STR-PEG2000/Chol-GALA (in FIG. 1, abbreviated as "GALA-Liposome"). Furthermore, when preparing a lipid membrane disclosed as "Cationic-Liposome" in FIG. 1, DOTMA (EtOH solution), Chol, and EPC were added at a molar ratio of 30/40/30, and an operation similar to that described above was conducted to prepare a lipid membrane (liposome b) whose lipid composition was DOTMA/Chol/EPC.

2) Liposome Preparation

To the lipid membrane prepared in 1) described above, 10 mM HEPES buffer with 5% Glucose (HBG) (in vivo experiment) or 10 mM HEPES buffer (HB) (in vitro experiment) was added to obtain a lipid concentration of 2.64 mM (in vivo experiment) or 0.55 mM (in vitro experiment), and hydration was conducted at room temperature for 15 minutes or longer. Then, a liposome was prepared through ultrasonication of approximately 1 minute in a bathtub type sonicator.

Example 2

Pharmacokinetic Evaluation of Liposome

1) Administration of Liposome, Organ Collection, and Measurement of [$^3$H]

A lipid membrane of the liposome prepared in 2) described above was labeled with [$^3$H] to obtain an administration sample.

Administration was conducted at a condition of 10 μL Liposome/g mouse to the tail veins of mice (ICR, 5 weeks of age, male). Mice were etherized 1, 5, and 15 minutes, and 1 and 6 hours after administration, had laparotomy performed thereon, had their blood drawn from the inferior vena cava, and had their lungs and livers removed. The organs were each rinsed thoroughly with saline solution, weighed (for livers, the livers were shredded, mixed thoroughly, and 0.2 g of the liver were used), placed in a plastic vial, and 2 mL of Soluene-350 was added thereto and the solution was incubated overnight at 50° C. to dissolve the tissue. The solution had 10 mL of Hionic fluor added thereto, mixed thoroughly, left still overnight at 4° C., and had a [$^3$H] count thereof measured using a liquid scintillation counter. Furthermore, in order to evaluate the administration dose of [$^3$H], 10 mL of Hionic fluor was added to 10 μL of the administered liposome sample, and the mixture was mixed thoroughly. The mixture was left still overnight at 4° C. and a [$^3$H] count was measured similarly.

2) Evaluation of Organ Migration Amount

The [$^3$H] count (measured value) of each organ sample was divided with the weight of the organ provided for the measurement to calculate the [$^3$H] contained per 1 g of each organ, and then this was divided with [$^3$H] contained in the administered liposome to calculate an organ migration amount as a ratio with respect to the administration dose.

The evaluation results of the lung and liver migration of GALA-modified liposome (GALA-Liposome) over time are shown in FIG. 1-A, FIG. 1-B, and FIG. 2.

As shown in FIG. 1-A, FIG. 1-B, and FIG. 2, the liposome modified with GALA was observed to migrate to the lung. In addition, it was confirmed that migration to the liver had reduced due to improvement in lung migration of the liposome modified with GALA.

Example 3-1

MEND1 Preparation

1) Lipid Membrane Preparation

Similarly to the method in Example 1, in a glass test tube, DOTMA (EtOH solution), Chol (EtOH solution), and EPC (EtOH solution) were added at a molar ratio of 30/40/30, a suitable amount of EtOH was added thereto, and the test tube was dried under reduced pressure in a desiccator to distill off solvents to prepare a lipid membrane (liposome b) whose lipid composition was DOTMA/Chol/EPC. When conducting the modification with STR-PEG2000 (EtOH solution), 5 mol % thereof with respect to the total lipid amount of liposome b was added to the lipid solution to prepare a lipid membrane whose lipid composition was DOTMA/Chol/EPC/STR-PEG2000 (hereinafter, sometimes abbreviated as "MEND1"). When conducting the modification with Chol-GALA, 2 mol % thereof with respect to the total lipid amount of liposome b was added to the lipid solution to prepare a lipid membrane whose lipid composition was DOTMA/Chol/EPC/STR-PEG2000/Chol-GALA (hereinafter, sometimes abbreviated as "GALA-MEND1").

2) Preparation of siRNA Complex (siRNA Core Particle)

A PEI/siRNA Complex was Prepared Such that a Charge ratio (+/−)=1.8 was obtained. It was prepared by dripping in 0.125 mg/mL of a PEI solution with respect to 0.333 mg/mL of a siRNA solution (volume ratio of siRNA solution:PEI solution=6:4) while having the solution placed in a vortex, and the solution was incubated for 15 minutes or longer at room temperature. As the siRNA solution and the PEI solution, those diluted with HBG were used.

3) Preparation of MEND

The siRNA core particle solution was added to the test tube in which the lipid membrane obtained in 1) described above was prepared such that the lipid concentration was 2.64 mM, and hydration was conducted at room temperature for 15 minutes or longer. Then, ultrasonication was conducting thereon in a bathtub type sonicator for approximately 1 minute to prepare MEND, and GALA-MEND1 and MEND1 encapsulating the siRNA core particle were created.

Example 3-2

Preparation of MEND2

1) Preparation of Lipid Membrane

Based on the preparation method described in Example 1, in a glass test tube, DODAP (EtOH solution), Chol (EtOH solution), and EPC (EtOH solution) were added at a molar ratio of 30/40/30 to prepare a lipid solution (liposome c) whose components are DODAP/Chol/EPC. To the obtained lipid solution, 5 mol % of STR-PEG2000 (EtOH solution) was added with respect to the total lipid amount of liposome c to prepare a lipid membrane whose lipid composition was DODAP/Chol/EPC/STR-PEG2000 (hereinafter, sometimes abbreviated as "MEND2"). When conducting the modification with Chol-GALA, 2 mol % thereof with respect to the total lipid amount of liposome c was added to the lipid solution of MEND2, a suitable amount of EtOH was added thereto, and the test tube was dried under reduced pressure in a desiccator to distill off solvents to prepare a lipid membrane whose lipid composition was DODAP/Chol/EPC/STR-PEG2000/Chol-GALA (hereinafter, sometimes abbreviates as "GALA-MEND2").

2) Preparation of siRNA Complex (siRNA Core Particle)

A PEI/siRNA complex was prepared such that a charge ratio (+/−)=1.8 was obtained. It was prepared by dripping in 0.125 mg/mL of a PEI solution with respect to 0.333 mg/mL of a siRNA solution (volume ratio of siRNA solution:PEI solution=6:4) while having the solution placed in a vortex, and the solution was incubated for 15 minutes or longer at room temperature. As the siRNA solution and the PEI solution, those diluted with HBG (pH unadjusted (pH 5.0)) were used to prepare the acidic-solution core particle.

3) Preparation of MEND

The siRNA core particle solution was added to the test tube in which the lipid membrane obtained in 1) described above was prepared such that the lipid concentration was 2.64 mM, and hydration was conducted at room temperature for 15 minutes or longer. Then, ultrasonication was conducting thereon in a bathtub type sonicator for approximately 1 minute and HBG (pH 8.1) was added by an equal amount of the siRNA core particle solution such that the prepared solution became neutral to prepare MEND, and GALA-MEND2 and MEND2 encapsulating the siRNA core particle were created.

Example 4

Interaction with Hemocyte

Mouse blood (containing heparin by 20 units/mL) and GALA-MEND1 solution were mixed at a volume ratio of 1:1, and the mixture was mixed using a shaker at 37° C. for 5 minutes (sample 1). Blood was further added to this mixture at a volume ratio of 10:1, and the mixture was mixed using the same condition (sample 2). 10 μL each of samples 1 and 2 was added on a slide glass, a coverslip was placed thereon, and the samples were observed using a microscope.

FIG. 3 shows the results of mixing blood and the obtained GALA-MEND1 at various ratios to evaluate interaction thereof with hemocyte components.

As shown in FIG. 3, it was observed that the aggregation of GALA-modified MEND and blood was reversible.

Example 5

Pharmacokinetic Evaluation of MEND

The lipid membrane of MEND was labeled with [$^3$H], and siRNA was labeled with [$^{32}$P] to obtain an administration sample.

MEND1 or GALA-MEND1 solution (2 mg siRNA/kg mouse) was administered to the tail veins of mice (ICR, 5 weeks of age, male). Mice were etherized 1 hour after administration, had laparotomy performed thereon, had their blood collected from the inferior vena cava, and had their lungs removed. The lungs were weighed, about 0.1 mg thereof was placed in a plastic vial, and 2 mL of Soluene-350 was added thereto and the solution was incubated overnight at 50° C. to dissolve the tissue.

To this solution, 200 μL (100 μL×2) of $H_2O_2$ was added for decolorization, 10 mL of Hionic fluor was added thereto, and the mixture was mixed thoroughly. The mixture was left still overnight at 4° C., and counts of [$^3$H] and [$^{32}$P] were measured using a liquid scintillation counter. Furthermore, a standard curve was created by adding a known amount of the MEND1 solution to a lung removed from an unadministered mice and performing the similar operation, and migration amounts of [$^3$H] and [$^{32}$P] to each organ were calculated.

Figure 4:
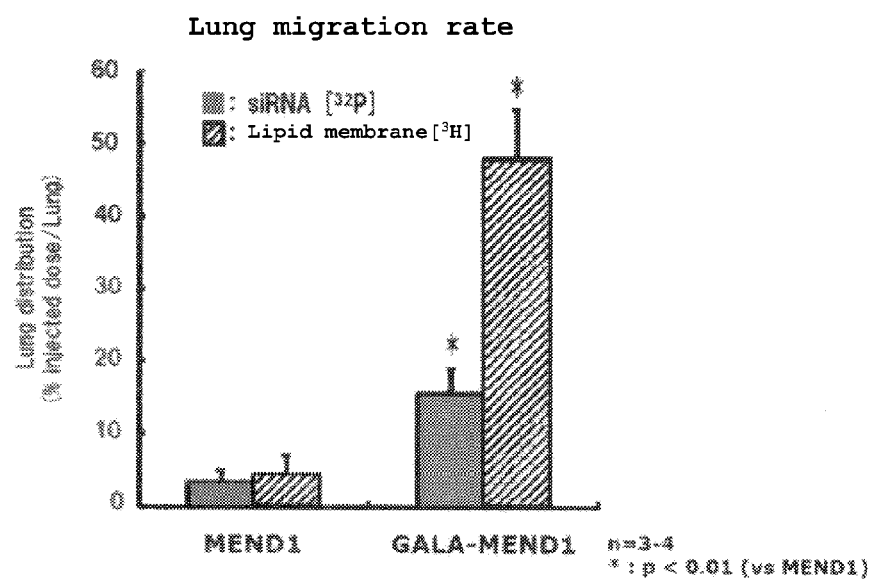
FIG. 4 shows the result of tail-vein intravenous administration of a GALA-modified MEND in which siRNA was labeled with [$^{32}$P] and lipid membrane was labeled with [$^{3}$H], and measuring [$^{32}$P] and [$^{3}$H] in the lung 1 hour after administration to evaluate migration of the GALA-modified MEND to the lung.

FIG. 4 shows the result of tail-vein intravenous administration of GALA-MEND1 or MEND1 in which siRNA was labeled with [$^{32}$P] and lipid membrane was labeled with [$^3$H], and measuring [$^{32}$P] and [$^3$H] in the lung 1 hour after administration to evaluate migration of the GALA-modified MEND to the lung.

As shown in FIG. 4, migration of MEND1 to the lung had improved significantly through GALA modification.

Example 6

Intra-Lung Localization of MEND with CLSM

MEND1 and GALA-MEND1 prepared using Cy5 labeled siRNA were used as administration samples.

MEND1 or GALA-MEND1 solution (2 mg siRNA/kg mouse) obtained in Example 3-1 was administered to the tail veins of mice (ICR, 5 weeks of age, male). Mice were anesthetized 1 hour after the tail-vein intravenous administration, and had their lung removed to create pieces of lung tissues of about several millimeters. The created pieces of lung tissues were placed in a GSL I-B4 Isolectin FITC conjugate (manufactured by Funakoshi Corp.) solution (diluted to be 20 μg/mL using saline solution) for 30 minutes to allow the solution to permeate therethrough, and were observed with CLSM.

FIG. 5 shows the result of tail-vein intravenous administration of MEND1 or GALA-MEND1 encapsulating fluorescent labeled siRNA, and evaluating localization of the GALA-modified MEND in the lung 1 hour after administration using a confocal laser scanning microscope.

As shown in FIG. 5, GALA-modified MEND was observed to be accumulated highly in the lung and to be co-localized with vascular endothelial cells.

Example 7-1

In Vivo Knockdown Effect Depending on Presence or Absence of GALA Modification

Knockdown effect of having GALA modification was investigated by using GALA-modified MEND and GALA-unmodified MEND.

1) Preparation of MEND Solution

Using a method similar to that in Example 3-1, a GALA-MEND1 solution and a GALA-unmodified MEND1 solution were prepared. More specifically, MEND1 was obtained by modifying a liposome prepared to have a lipid composition of DOTMA/Chol/EPC=30/40/30, using 5 mol % of STR-PEG2000 with respect to the total lipid amount of the liposome; and GALA-MEND1 was obtained by further modifying MEND1 using 2 mol % of Chol-GALA with respect to the total lipid amount.

2) In Vivo Transfection

The MEND solutions (0.5-4 mg siRNA/kg mouse) obtained in 1) described above were administered to the tail veins of mice (C57BL/6, 6w, male). Mice were etherized 24 hours after the tail-vein intravenous administration, had laparotomy perform thereon, and had their respective organs (lung, liver, and spleen) removed. The removed organs were dipped in RNAlater, kept at 4° C. overnight, and stored at −20° C.

3) mRNA Extraction

The organ samples stored at −20° C. were returned to room temperature, had their weight adjusted to 20-30 mg, and were used for RNA extraction using RNA mini kit and QIA cube (manufactured by Qiagen in accordance with attached protocols.

4) Reverse Transcription cDNA was prepared from 1 μg of total RNA using High Capacity RNA-to-cDNA Kit in accordance with an attached protocol. Denature and reverse transcription were conducted using a thermal cycler with conditions of denature (65° C., 5 min=>4° C. hold) and reverse transcription (42° C., 60 min=>95° C., 5 min=>4° C., hold).

5) mRNA Quantification Using Real-Time PCR

Quantification of mRNA (CD31) was conducted using relative quantification method (delta-delta Ct method) based on TaqMan method. With respect to 5 μL of cDNA diluted to an intended concentration, 0.25 μL of 100 μM Upper Primer, 0.25 μL of 100 μM Lower Primer, 0.0625 μL of 100 μM probe, 6.9375 μL of filtrated DDW, and 12.5 μL of 2× TaqMan M.M., were added. Then, the initial denaturation was conducted at 95° C. for 10 min, PCR denaturation reaction was conducted at 95° C. for 15 sec, and 40 cycles of PCR was conducted in which the annealing/extension reaction was conducted as a single cycle of 60° C. for 1 min. By using CD34 as an internal standard gene, mRNA level of CD31 was calculated from relative quantification using delta-delta Ct method.

FIG. 6 shows the result of tail-vein intravenous administration of GALA-MEND1 and MEND1, and evaluation of the respective knockdown effects of GALA-MEND1 and MEND1 in the lung 24 hours after administration using qRT-PCR. It should be noted that, in FIG. 6, GALA (+) shows the result of GALA-MEND1, and GALA (−) shows the result of MEND1.

As shown in FIG. 6, the knockdown effect in the lung was significantly improved by modifying MEND with GALA.

Example 7-2

In Vivo Knockdown Evaluation

1) By using a method similar to that in Example 7-1 of in vivo transfection, mRNA extraction, reverse transcription, and mRNA quantification with real-time PCR; GALA-modified MEND (whose lipid composition in molar ratio was DOTMA/Chol/EPC=30/40/30, and whose GALA modification level was 2 mol % with respect to the total lipid amount) created with a method similar to that of Example 3-1, was intravenously administered through the tail veins, and the knockdown effect of GALA-modified MEND in the lung, liver, and spleen 24 hours after administration was evaluated with qRT-PCR.

Figure 7:
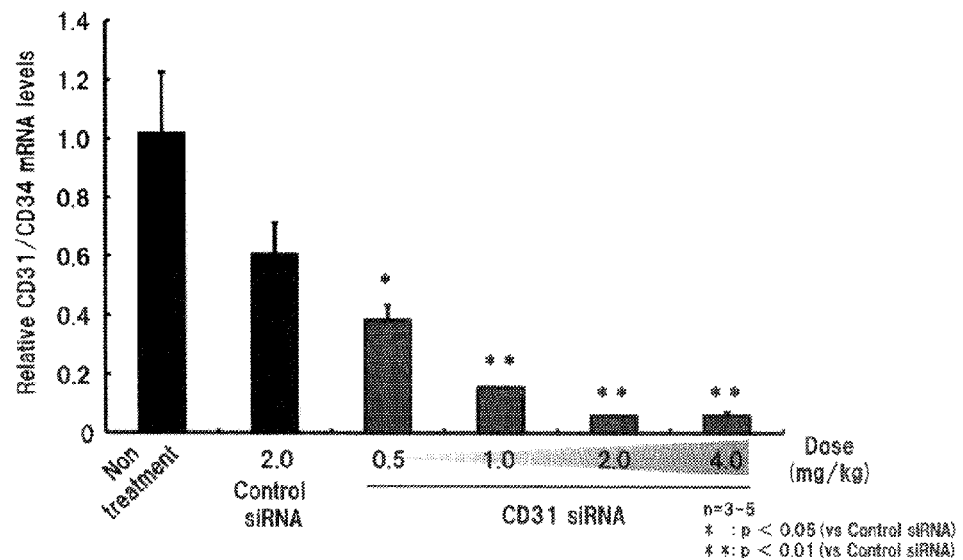
FIG. 7 shows the result of tail-vein intravenous administration of a GALA-modified MEND, and evaluating the knockdown effect of the GALA-modified MEND in the lung 24 hours after administration using qRT-PCR.

FIG. 7 shows the result of tail-vein intravenous administration of the GALA-modified MEND, and evaluation of the knockdown effect of GALA-modified MEND in the lung 24 hours after administration using qRT-PCR.

Figure 8:
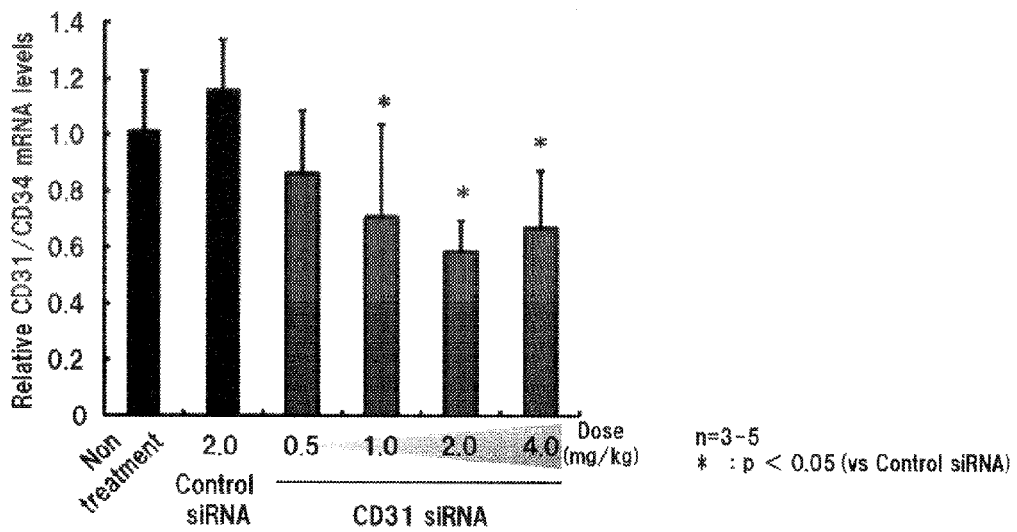
FIG. 8 shows the result of tail-vein intravenous administration of a GALA-modified MEND, and evaluating the knockdown effect of GALA-modified MEND in the liver 24 hours after administration using qRT-PCR.

FIG. 8 shows the result of tail-vein intravenous administration of the GALA-modified MEND, and evaluation of the knockdown effect of the GALA-modified MEND in the liver 24 hours after administration using qRT-PCR.

Figure 9:
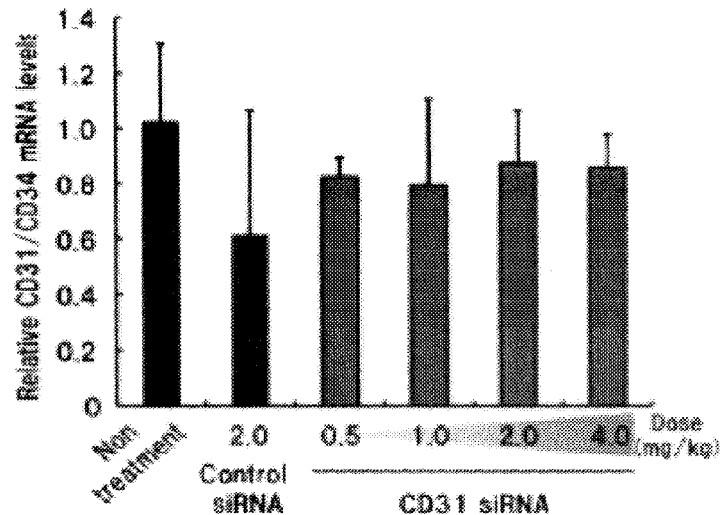
FIG. 9 shows the result of tail-vein intravenous administration of a GALA-modified MEND, and evaluating the knockdown effect of the GALA-modified MEND in the spleen 24 hours after administration using qRT-PCR.

FIG. 9 shows the result of tail-vein intravenous administration of the GALA-modified MEND, and evaluation of the knockdown effect of the GALA-modified MEND in the spleen 24 hours after administration using qRT-PCR.

As shown in FIG. 7, when compared to AtuPLEX which is an existing carrier, the GALA-modified MEND showed a significantly stronger knockdown effect in the lung.

As shown in FIG. 8, when compared to AtuPLEX which is an existing carrier, although the GALA-modified MEND showed a knockdown effect in the liver when 1.0-4.0 mg/kg thereof was administered, when compared to FIG. 7, the knockdown effect in the lung was much stronger than that in the liver.

Furthermore, as shown in FIG. 9, the GALA-modified MEND did not show any significant knockdown effect in the spleen.

Example 7-3

Knockdown Effects of MENDs Having Different Cationic Lipids

GALA-MENDs having different cationic lipids were prepared, and the knockdown effects of each of the GALA-MENDs were compared.

1) Preparation of MENDs

Preparation of GALA-MEND1 (whose lipid composition was DOTMA/Chol/EPC/STR-PEG2000/Chol-GALA) using DOTMA as a cationic lipid was conducted by a method similar to that in Example 3-1. Preparation of GALA-MEND3 (whose lipid composition was DSTAP/Chol/EPC/STR-PEG2000/Chol-GALA) using DSTAP as a cationic lipid was conducted based on the preparation method described in Example 3-1, except for changing DOTMA to DSTAP. Furthermore, preparation of GALA-MEND2 (whose lipid composition was DODAP/Chol/EPC/STR-PEG2000/Chol-GALA) using DODAP as a cationic lipid was conducted by a method similar to that in Example 3-2.

2) In Vivo Knockdown Evaluation

Knockdown effects of each of the GALA-MENDs having different cationic lipids obtained in 1) described above were evaluated. The evaluation was conducted with a method similar to that in Example 7-1.

Figure 10:
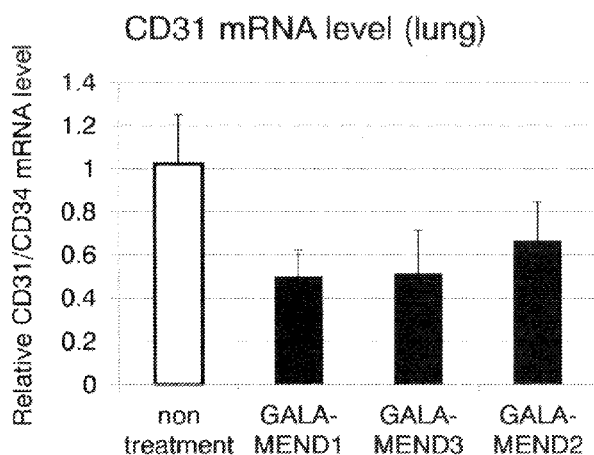
FIG. 10 shows the knockdown effect of MEND when DOTMA, DSTAP, and DODAP are used as a cationic lipid.

FIG. 10 shows the knockdown effects of GALA-MENDs 1 to 3 when DOTMA, DODAP, and DSTAP are used as a cationic lipid. It should be noted that the administration dose was 0.5 mg siRNA/kg.

As shown in FIG. 10, no matter whether the cationic lipid was a tertiary amine or a quaternary amine, it was shown that the MENDs according to the present invention had high knockdown effects. Among those, it was shown that the MEND having DOTMA as a cationic lipid had the highest knockdown effect.

Example 7-4

Knockdown Effects of MENDs Having Different Helper Lipids

MENDs having different helper lipids were prepared, and the knockdown effects of each of the MENDs were compared.

1) Preparation of MENDs

Preparation of MENDs including helper lipids was conducted with a method similar to that of Example 3-1. More specifically, liposomes having DOTMA/Chol/Helper lipid by a molar ratio of 30/40/30 were prepared, and then GALA-modified MENDs were prepared by modifying the liposomes with 5 mol % of STR-PEG2000 and 2 mol % of Chol-GALA with respect to the total lipid amount of the each of the liposomes.

2) In Vivo Knockdown Evaluation

Knockdown effects of each of the GALA-modified MENDs having different helper lipids were evaluated. The evaluation was conducted with a method similar to that in Example 7-1.

Figure 11:
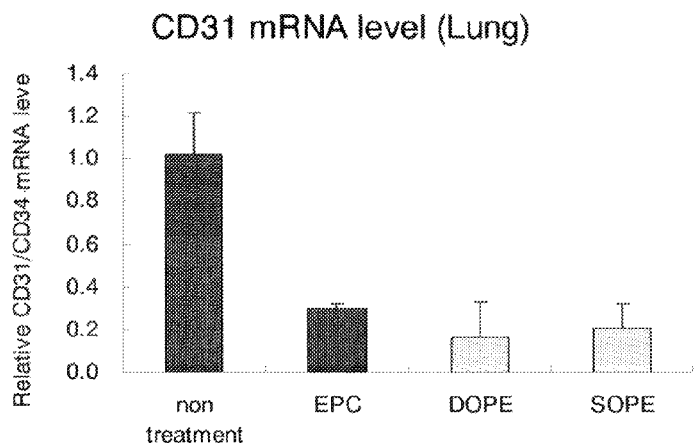
FIG. 11 shows the knockdown effects of the respective MENDs when EPC, DOPE, and SOPE are used as a helper lipid.

FIG. 11 shows the knockdown effects of the each of the GALA-modified MENDs when EPC, DOPE, and SOPE were used as a helper lipid. It should be noted that, in FIG. 11, "EPC," "DOPE," and "SOPE" respectively show GALA-modified MENDs whose lipid compositions are DOTMA/Chol/EPC/STR-PEG2000/Chol-GALA, DOTMA/Chol/DOPE/STR-PEG2000/Chol-GALA, and DOTMA/Chol/SOPE/STR-PEG2000/Chol-GALA. Furthermore, the administration dose was 0.5 mg siRNA/kg.

As shown in FIG. 11, regardless of the type of helper lipid, it was shown that the GALA-modified MENDs according to the present invention including the helper lipids had high knockdown effects.

Example 8-1

Weight Change from Continuous Administration of MEND for 4 Days

1) Preparation of MEND Solution

A GALA-modified MEND solution was prepared according to the method in Example 3-1. More specifically, the lipid composition was set to be DOTMA/Chol/EPC=30/40/30 (molar ratio), and the GALA modification level with respect to the total lipid amount was set as 2 mol %.

The GALA-modified MEND solution created in 1) described above was administered (using a hypodermic needle of 27G) continuously for 4 days in the tail veins of mice (C57BL/6, 6w, male). The weight of each of the mice was measured every day from the administration start day to one day after the final administration, and weight changes thereof due to continuous administration were calculated. It should be noted that the administration dose was 1 or 2 mg siRNA/kg/day.

Figure 12:
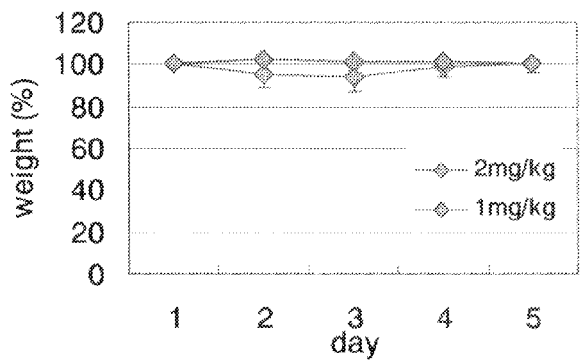
FIG. 12 shows a change in weight when a GALA-modified MEND is continuously administered for 4 days.

FIG. 12 shows weight change when a GALA-modified MEND is continuously administered for 4 days.

As shown in FIG. 12, weight reduction was not observed when 1 or 2 mg/kg of the GALA-modified MEND of the present invention was continuously administered for 4 days.

Example 8-2

AST and ALT after Continuous Administration of MEND for 4 Days

Mice were intravenously administered the GALA-modified MEND used in Example 8-1 through their tail veins continuously for 4 days, etherized and had laparotomy performed thereon 24 hours after the final administration to have their blood collected from the caudal vena cava using a 23G hypodermic needle and a 1 mL syringe. The blood was left still for 4 hours at 4° C., and centrifuged (4° C., 12000 rpm, 2 min) to collect its supernatant as a serum. AST and ALT in the serum were measured using 5 μL of the serum and an AST and ALT measurement kit (transaminase CII-Test Wako) with a method attached therein. The results are shown in FIG. 13.

Figure 13:
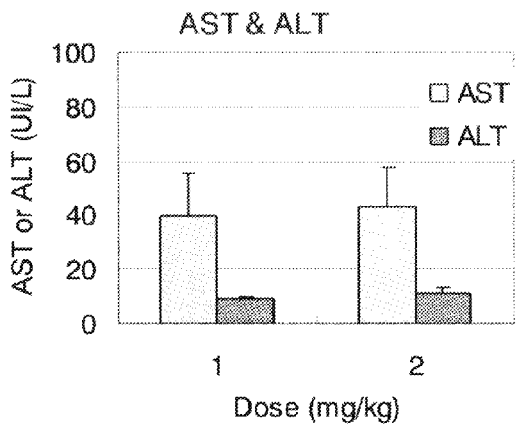
FIG. 13 shows a measurement result of AST and ALT when MEND is continuously administered for 4 days.

As shown in FIG. 13, since changes were not been observed in AST and ALT, the GALA-modified MEND according to the present invention was considered not to cause liver damage a day after the 4-day continuous administration.

Example 9

Pharmacokinetic Evaluation of PEG-Modified MEND

Pharmacokinetics of the GALA-modified MEND depending on presence or absence PEG modification were compared using a PEG-unmodified/GALA-modified MEND and a PEG-modified/GALA-modified MEND.

The MEND created with the method in Example 3-1 was used. The PEG modification level with respect to the total lipid amount was set as 1 mol % or 5 mol %.

The pharmacokinetic evaluation of MEND was conducted according to Example 5. It should be noted that, the pharmacokinetic evaluations were conducted by N=2 for PEG-unmodified MEND (lipid composition: DOTMA/Chol/EPC), 1% STR-PEG2000-modified MEND (lipid composition: DOTMA/Chol/EPC/STR-PEG2000), and 1% C8 ceramide-PEG2000-modified MEND (lipid composition: DOTMA/Chol/EPC/C8 ceramide-PEG2000).

Figure 14:
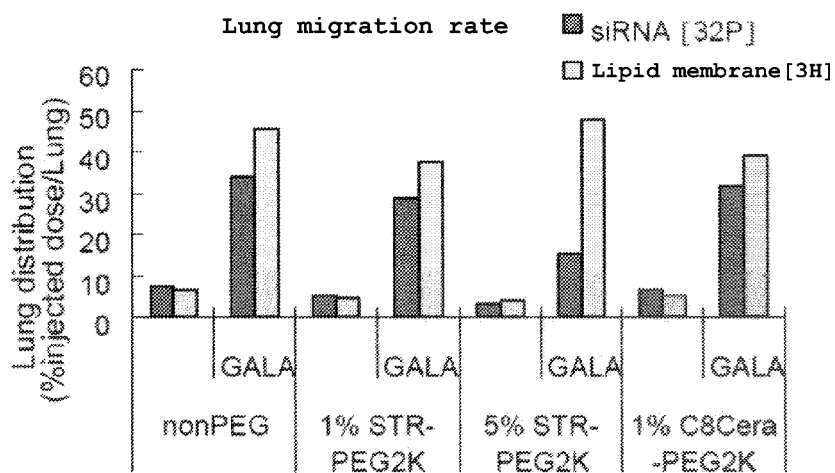
FIG. 14 shows the result of a pharmacokinetic evaluation of a PEG-modified MEND.

FIG. 14 shows a comparison of lung migration rates of the PEG-unmodified/GALA-modified MEND (lipid composition: DOTMA/Chol/EPC/Chol-GALA), and the PEG-modified/GALA-modified MEND (lipid composition: DOTMA/Chol/EPC/STR-PEG2000/Chol-GALA and DOTMA/Chol/EPC/C8 ceramide-PEG2000/Chol-GALA).

As shown in FIG. 14, a high level of lung migration was observed even when GALA-modified MEND was modified with STR-PEG and C8 ceramide-PEG.

Example 10

Knockdown Effect of PEG-Modified MEND

Knockdown effects of the GALA-modified MEND depending on presence or absence of PEG modification were compared using the PEG-unmodified/GALA-modified MEND and the PEG-modified/GALA-modified MEND.

Figure 15:
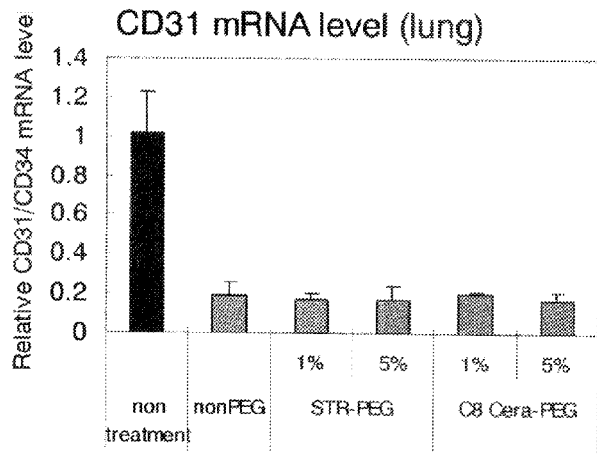
FIG. 15 shows the knockdown effect of a PEG-modified MEND.

As the MEND, the PEG-unmodified/GALA-modified MEND and the PEG-modified/GALA-modified MEND used in Example 9 were used. More specifically, STR-PEG2000 and C8 ceramide-PEG2000 were used as PEG, and the PEG modification level with respect to the total lipid amount was 1 mol % and 5 mol %. A method similar to that in Example 7-1 was used for knockdown evaluation by MEND. It should be noted that the administration dose was 1 mg siRNA/kg. FIG. 15 shows a comparison of the knockdown effects of the PEG-unmodified/GALA-modified MEND and the PEG-modified/GALA-modified MEND.

As shown in FIG. 15, a high knockdown effect was obtained even when the GALA-modified MEND was modified with STR-PEG2000 and C8 ceramide-PEG2000; and it was possible to suppress aggregation of the GALA-modified MEND through PEG modification.

Example 11

Knockdown Effect of PEG-Modified MEND after being Stored for Certain Period of Time Next, the knockdown effects of the PEG-unmodified/GALA-modified MEND and the PEG-modified/GALA-modified MEND were compared after being stored for a certain period of time.

Figure 16:
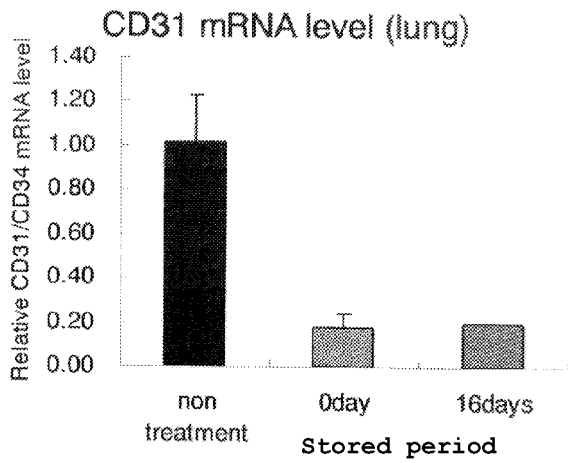
FIG. 16 shows the knockdown effect of a stored MEND article.

As the GALA-modified MEND, the PEG-unmodified/GALA-modified MEND and the PEG-modified/GALA-modified MEND used in Example 9 were used. It should be noted that STR-PEG2000 was used as PEG, and the PEG modification level with respect to the total lipid amount was 5 mol %. The MENDs were stored for 16 days at room temperature in HBG solution (pH 7.4). A method similar to that in Example 7-1 was used for the knockdown evaluation of the MENDs. It should be noted that the administration dose was 1 mg siRNA/kg. The knockdown evaluation of the 16 day-stored MENDs was conducted by N=2. FIG. 16 shows the knockdown effects of the PEG-unmodified/GALA-modified MEND and the PEG-modified/GALA-modified MEND stored at room temperature for 16 days.

As shown in FIG. 16, it was shown that the STR-PEG2000-modified/GALA-modified MEND had high knockdown effect in the lung even after being stored at room temperature for 16 days.

Example 12

Storage Stability of GALA-Modified MEND

Next, the influence of changing the helper lipid on physical properties of the GALA-modified MEND was examined using presence or absence of aggregation of the GALA-modified MEND after being kept at room temperature for 1 month.

Figure 17:
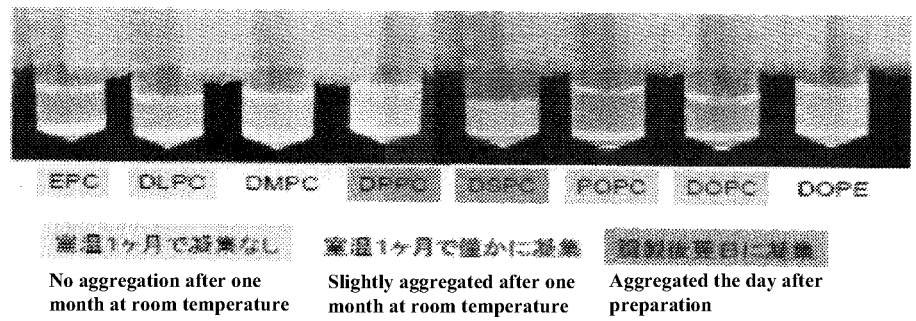
FIG. 17 shows the result of storage stability of a GALA-modified MEND after it is stored for 1 month at room temperature.

The used GALA-modified MEND was created by the method in Example 3-1, a method based thereon, or a combination of those and a method commonly used in the art. The MEND was stored in HBG solution for 1 month at room temperature. Characteristics of the MEND after being kept at room temperature for 1 month are shown in FIG. 17. It should be noted that, in FIG. 17, "EPC," "DLPC," "DMPC," "DPPC," "DSPC," "POPC," "DOPC," and "DOPE" respectively show liposomes having lipid compositions of DOTMA/Chol/EPC/STR-PEG2000/Chol-GALA, DOTMA/Chol/DLPC/STR-PEG2000/Chol-GALA, DOTMA/Chol/DMPC/STR-PEG2000/Chol-GALA, DOTMA/Chol/DPPC/STR-PEG2000/Chol-GALA, DOTMA/Chol/DSPC/STR-PEG2000/Chol-GALA, DOTMA/Chol/POPC/STR-PEG2000/Chol-GALA, DOTMA/Chol/DOPC/STR-PEG2000/Chol-GALA, and DOTMA/Chol/DOPE/STR-PEG2000/Chol-GALA.

As shown in FIG. 17, when EPC, DLPC, POPC, or DOPC was used as the helper lipid, aggregation of the GALA-modified MEND was not observed after being kept at room temperature for 1 month; and when DOPE was used as the helper lipid, only slight aggregation of the GALA-modified MEND was observed after being kept at room temperature for 1 month.

Example 13

Influence of GALA Modification Level on In Vivo Knockdown

Figure 18:
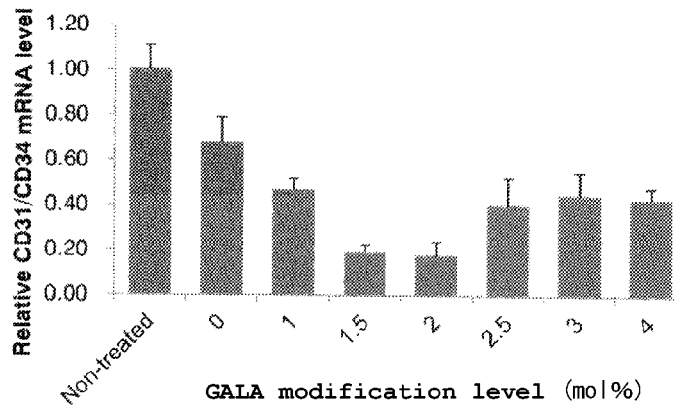
FIG. 18 shows the result of tail-vein intravenous administration of MENDs with different GALA modification levels, and evaluating the knockdown effect of the GALA-modified MENDs in the lung 24 hours after administration using qRT-PCR.

By using MENDs having different GALA modification levels, the influence of GALA modification level on the knockdown effect was evaluated. More specifically, by using a method similar to that in Example 7-1 of in vivo transfection, mRNA extraction, reverse transcription, and mRNA quantification with real-time PCR; GALA-modified MENDs, (whose lipid composition in molar ratio was DOTMA/Chol/EPC=30/40/30, and, with respect to the total lipid amount of the liposome, whose STR-PEG2000 modification level was 5 mol % and whose GALA modification levels were 1 to 4 mol %) created with a method similar to that of Example 3-1, were intravenously administered through the tail veins, and the knockdown effects of the GALA-modified MENDs in the lung 24 hours after administration were evaluated with qRT-PCR. FIG. 18 shows the result of tail-vein intravenous administration of MENDs with different GALA modification levels, and evaluating the knockdown effects of each of the MENDs with different GALA modification levels in the lung 24 hours after administration using qRT-PCR.

As shown in FIG. 18, the knockdown effect in the lung was improved through GALA modification of 1 to 4 mol %, and, in particular, the knockdown effect in the lung had the highest improvement through GALA modification of 1.5 to 2 mol %.

Example 14

Antitumor Effect of MEND Administration in Melanoma Pulmonary Metastasis Cancer Model 1) Preparation of MEND Solutions Using a method similar to that in Example 3-1, a GALA-modified MEND solution and a GALA-unmodified MEND solution were prepared. Their lipid composition in molar ratio was DOTMA/Chol/EPC=30/40/30, and, with respect to the total lipid amount of the liposome, the STR-PEG2000 modification level was 5 mol % and the GALA modification level was 2 mol %.

2) Creating a Model for Melanoma Pulmonary Metastasis Cancer

Luciferase (GL4) stable expression B16-F10 mouse melanoma cells (B16-F10-luc2: Caliper Life Sciences, MA, USA) were cultured for 48 hours in an RPMI-1640 medium containing 10% FBS. Mice (C57BL/6, 6w, male) were administered the B16-F10-luc2 cells ($2 \times 10^5$ cells/100 µL) through their tail veins to create a melanoma pulmonary metastasis cancer model (day 0).

3) MEND Administration to Melanoma Pulmonary Metastasis Cancer Model

GALA-modified MEND encapsulating control siRNA (anti-Luc (GL3)) or anti-CD31 siRNA was administered (1 mg siRNA/KG mouse) to the model mice every three days from the next day after transplantation of the B16-F10-luc2 cells. The mice had laparotomy performed thereon 17 days after transplantation of tumor, and had their lungs removed. The removed lungs were each divided into two, one for tumor pulmonary metastasis evaluation and one for evaluation of CD31 mRNA expression level. It should be noted that the body weight of the mice was monitored during the MEND administration period.

4) Quantitative Evaluation of Tumor Pulmonary Metastasis

The removed pulmonary sample was placed in an assist tube, had 1 mL of in vivo lysis buffer added thereto, and was homogenized using a POLYTRON homogenizer (manufactured by KINEMATICA AG). The homogenate was recovered in a sample tube and centrifuged (4° C., 13,000 rpm, 10 minutes). 50 µL of Luciferase assay substrate was mixed with 20 µL of the supernatant, and luciferase activity was measured using a luminometer (Luminescencer-PSN, manufactured by ATTO Corp.). The luciferase activity (RLU/lung) was calculated as relative light units (RLU) with respect to the whole lung. The results are shown in FIG. 19.

5) CD31 mRNA Expression Level Evaluation

Figure 20:
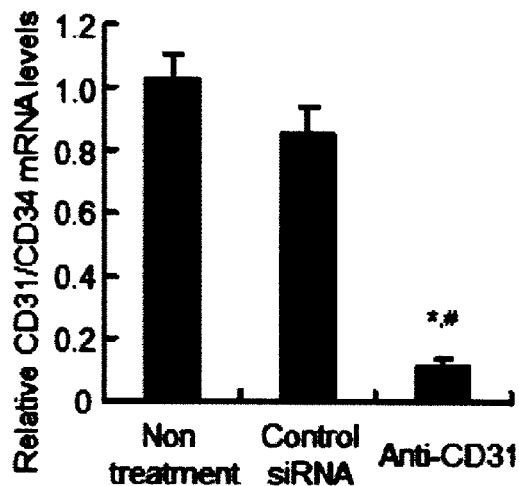
FIG. 20 shows the knockdown effect of administering a GALA-modified MEND in a pulmonary metastasis model.

By using a method similar to that in Example 7-1, the CD31 mRNA levels in the removed lungs were calculated. The result is shown in FIG. 20.

Figure 19:
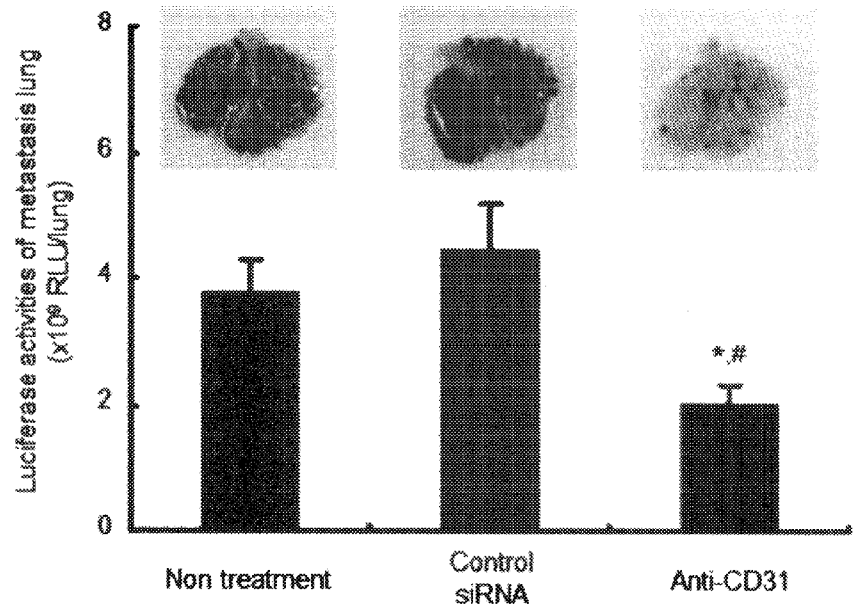
FIG. 19 shows the pulmonary metastasis suppression effect of administering a GALA-modified MEND in a pulmonary metastasis model.

As shown in FIG. 19, by administering the GALA-modified MEND encapsulating anti-CD31 siRNA, progress of pulmonary metastasis was suppressed significantly when compared to untreated group and control siRNA administered group. Furthermore, as shown in FIG. 20, by administering the GALA-modified MEND encapsulating anti-CD31 siRNA, CD31 mRNA expression level was significantly suppressed when compared to untreated group and control siRNA administered group.

Hitherto, it has been reported that knocking out CD31 or administering anti CD31 antibody inhibits angiogenesis in tumor tissues, resulting in suppression of progression of melanoma pulmonary metastasis (Proc Natl Acad Sci USA. 2010 Oct. 26; 107(43):18616-21). The pulmonary metastasis progression suppression effect obtained from administering the GALA-modified MEND obtained here is thought to be attributed to inhibition of angiogenesis in pulmonary metastasis tumor tissues due to knockdown of CD31 mRNA.

It should be noted that, since weight reduction caused by administration of GALA-modified MEND to the model mouse for pulmonary metastasis has not been observed, it was suggested that the GALA-modified MEND can be used for treating pulmonary metastasis without exhibiting toxicity.

From these results, it was observed that a GALA-modified liposome migrates specifically to the lung.

Furthermore, it was observed that a GALA-modified liposome encapsulating siRNA has an efficient knockdown effect in the lung.

Furthermore, since weight reduction and liver damage were not observed even when the GALA-modified MEND of the present invention was administered, it was confirmed that the administration can be conducted safely.

From the results above, it became clear that the vector modified with the GALA peptide of the present invention is useful as a carrier for specifically delivering an intended substance to the lung, and as a carrier for specifically delivering preferably a medication, and more preferably a nucleic acid medicine such as siRNA to the lung.

The liposomes (MENDs) obtained in the Examples as a substance introduction agent had an average size of about 90 to 170 nm, and a zeta-potential within a range of −50 to 50 mV.

The sizes and zeta-potential of the liposomes prepared in Examples 1 and 3 are respectively shown in Table 2 and Table 3.

TABLE 2

Size and zeta-potential of liposomes prepared in Example 1.

| Type of Liposome | Lipid composition | Physicochemical properties | |
|---|---|---|---|
| | | Size (nm) | $\zeta$ potential (mV) |
| Liposome | EPC/Cholesterol = 7:3 | 100 ± 3 | −7 ± 1 |
| GALA-Liposome | EPC/Cholesterol = 7:3, GALA 2 mol % | 67 ± 3 | −23 ± 3 |

TABLE 3

Size and zeta-potential of MENDs prepared in Example 3.

| Type of Liposome | Lipid composition | | | Physicochemical properties | |
|---|---|---|---|---|---|
| | | | | Size (nm) | $\zeta$ potential (mV) |
| MEND | DOTMA/ Cholesterol/ EPC = 30:40:30 | | | 163 ± 3 | 36 ± 2 |
| GALA-MEND | DOTMA/ Cholesterol/ EPC = 30:40:30 | GALA 2 mol % | | 116 ± 8 | 23 ± 1 |
| PEG-MEND | DOTMA/ Cholesterol/ EPC = 30:40:30 | | STR-PEG2000 5 mol % | 146 | 29 |
| PEG-GALA-MEND | DOTMA/ Cholesterol/ EPC = 30:40:30 | GALA 2 mol % | STR-PEG2000 5 mol % | 107 ± 12 | 15 ± 1 |

Literature disclosed in the present specification is incorporated herein by reference in its entirety.

Sequence Listing

The invention claimed is:

1. A method for introducing an intended substance to a lung, the method comprising administering, to a mammal by intravenous injection, a vector that has encapsulated therein the intended substance and has bound thereto a GALA peptide represented by SEQ ID NO: 1 in an amount sufficient for accumulation in the lung to be more than accumulation in the liver, wherein the vector includes cholesterol and at least one helper lipid selected from the group consisting of egg phosphatidylcholine (EPC), dioleoylphosphatidylethanolamine (DOPE), stearyloleoylphosphatidylcholine (SOPE), dimyristoylphosphatidylcholine (DLPC), palmitoyloleoylphosphatidylcholine (POPC) and dioleoylphosphatidylcholine (DOPC).

2. The method according to claim 1, wherein the GALA peptide is bound to a cationic lipid and/or cholesterol.

3. The method according to claim 1, wherein the intended substance is selected from the group consisting of drugs, nucleic acids, peptides, proteins, sugars, and complexes thereof.

4. The method according to claim 1, wherein the vector includes a cationic lipid, and the cationic lipid includes at least one type selected from the group consisting of N-(2,3-dioleyloxy)propyl-N,N,N-trimethylammonium (DOTMA), 1,2-distearoyl-3-trimethylammonium propane (DSTAP), and dioleoyl-3-dimethylammonium-propane (DODAP).

5. The method according to claim 1, wherein the vector is modified with a hydrophilic polymer selected from the group consisting of polyalkylene glycol, dextran, pullulan, ficoll, polyvinyl alcohol, styrene-maleic anhydride alternating copolymer, divinyl ether-maleic anhydride alternating copolymer, amylose, amylopectin, chitosan, mannan, cyclodextrin, pectin, and carrageenan.

6. The method according to claim 1, further comprising a helper lipid, wherein the helper lipid is selected from the group consisting of egg phosphatidylcholine (EPC), dioleoylphosphatidylcholine (DOPC), dioleoylphosphatidylethanolamine (DOPE), and stearyloleoylphosphatidylcholine (SOPE).

7. The method according to claim 1, wherein: the vector is a liposome including, as a component of lipid membrane, N-(2,3-dioleyloxy)propyl-N,N,N-trimethylammonium (DOTMA), cholesterol (Chol), and egg phosphatidylcholine (EPC);

a lipid composition (molar ratio) of the liposome regarding N-(2,3-dioleyloxy) propyl-N,N,N-trimethylammonium (DOTMA)/cholesterol (Chol)/egg phosphatidylcholine (EPC) is 10 to 50/20 to 50/20 to 70; and the liposome further includes (stearyl)-polyethylene glycol with a molecular weight of 2000 (STR-PEG2000) by 1 to 15 mol % and Chol-GALA by 0.1 to 5 mol % with respect to the total lipid amount of N-(2,3-dioleyloxy)propyl-N,N,N-trimethylammonium (DOTMA)/cholesterol (Chol)/egg phosphatidylcholine (EPC).

8. A method for introducing an intended substance to a lung, the method comprising administering, to a mammal by intravenous injection, a vector that has encapsulated therein the intended substance and has bound thereto a GALA peptide represented by SEQ ID NO: 1 in an amount sufficient to improve lung migratability and reduce liver migratability compared to a vector without a GALA peptide, wherein the vector includes cholesterol and at least one helper lipid selected from the group consisting of egg phosphatidylcholine (EPC), dioleoylphosphatidylethanolamine (DOPE), stearyloleoylphosphatidylcholine (SOPE) dimyristoylphosphatidylcholine (DLPC), palmitoyloleoylphosphatidylcholine (POPC) and dioleoylphosphatidylehbline (DOPC).

9. The method according to claim 8, wherein the GALA peptide is bound to a cationic lipid and/or cholesterol.

10. The method according to claim 8, wherein the intended substance is selected from the group consisting of drugs, nucleic acids, peptides, proteins, sugars, and complexes thereof.

11. The method according to claim 8, wherein the vector includes a cationic lipid, and the cationic lipid includes at least one type selected from the group consisting of N-(2, 3-dioleyloxy)propyl-N,N,N-trimethylammonium (DOTMA), 1,2-distearoyl-3-trimethylammonium propane (DSTAP), and dioleoyl-3-dimethylammonium-propane (DODAP).

12. The method according to claim 8, wherein the vector is modified with a hydrophilic polymer selected from the group consisting of polyalkylene glycol, dextran, pullulan, ficoll, polyvinyl alcohol, styrene-maleic anhydride alternating copolymer, divinyl ether-maleic anhydride alternating copolymer, amylose, amylopectin, chitosan, mannan, cyclodextrin, pectin, and carrageenan.

13. The method according to claim 8, further comprising a helper lipid, wherein the helper lipid is selected from the group consisting of egg phosphatidylcholine (EPC), dioleoylphosphatidylcholine (DOPC), dioleoylphosphatidylethanolamine (DOPE), and stearyloleoylphosphatidylcholine (SOPE).

14. The method according to claim 8, the vector is a liposome including, as a component of lipid membrane, N-(2,3-dioleyloxy)propyl-N,N,N-trimethylammonium (DOTMA), cholesterol (Chol), and egg phosphatidylcholine (EPC);

a lipid composition (molar ratio) of the liposome regarding N-(2,3-dioleyloxy) propyl-N,N,N-trimethylammonium (DOTMA)/cholesterol (Chol)/egg phosphatidylcholine (EPC) is 10 to 50/20 to 50/20 to 70; and the liposome further includes (clearly stearyl)-polyethylene glycol with a molecular weight of 2000 (STR-PEG2000) by 1 to 15 mol % and Chol-GALA by 0.1 to 5 mol % with respect to the total lipid amount of N-(2,3-dioleyloxy)propyl-N,N,N-trimethylammonium (DOTMA)/cholesterol (Chol)/egg phosphatidylcholine (EPC).

* * * * *

```
                         SEQUENCE LISTING

<160> NUMBER OF SEQ ID NOS: 15

<210> SEQ ID NO 1
<211> LENGTH: 30
<212> TYPE: PRT
<213> ORGANISM: Artificial Sequence
<220> FEATURE:
<223> OTHER INFORMATION: Designed peptide called "GALA"

<400> SEQUENCE: 1

Ala Ala Leu Ala Glu Leu Ala Glu Ala Leu Ala Glu Ala Leu His Glu
1               5                   10                  15

Ala Leu Ala Glu Ala Leu Ala Glu Ala Leu Ala Ala Glu Trp
            20                  25                  30

<210> SEQ ID NO 2
<211> LENGTH: 21
<212> TYPE: DNA
<213> ORGANISM: Artificial Sequence
<220> FEATURE:
<223> OTHER INFORMATION: cd31-1 sense

<400> SEQUENCE: 2
gcacagugau gcugaacaat t                                            21

<210> SEQ ID NO 3
<211> LENGTH: 21
<212> TYPE: DNA
<213> ORGANISM: Artificial Sequence
<220> FEATURE:
<223> OTHER INFORMATION: CD31-1 antisense

<400> SEQUENCE: 3
uuguucagca ucacugugct t                                            21

<210> SEQ ID NO 4
<211> LENGTH: 21
<212> TYPE: DNA
<213> ORGANISM: Artificial Sequence
<220> FEATURE:
<223> OTHER INFORMATION: CD31-2 sense

<400> SEQUENCE: 4
gugcauaguu caagugacat t                                            21

<210> SEQ ID NO 5
<211> LENGTH: 21
<212> TYPE: DNA
<213> ORGANISM: Artificial Sequence
<220> FEATURE:
<223> OTHER INFORMATION: CD31-2 antisense

<400> SEQUENCE: 5
ugucacuuga acuaugcact t                                            21

<210> SEQ ID NO 6
<211> LENGTH: 21
<212> TYPE: DNA
<213> ORGANISM: Artificial Sequence
<220> FEATURE:
<223> OTHER INFORMATION: CD31-3 sense

<400> SEQUENCE: 6
gcaagaagca ggaaggacat t                                            21
```

<210> SEQ ID NO 7
<211> LENGTH: 21
<212> TYPE: DNA
<213> ORGANISM: Artificial Sequence
<220> FEATURE:
<223> OTHER INFORMATION: CD31-3

<400> SEQUENCE: 7
uguccuuccu gcuucuugct t                                              21

<210> SEQ ID NO 8
<211> LENGTH: 21
<212> TYPE: DNA
<213> ORGANISM: Artificial Sequence
<220> FEATURE:
<223> OTHER INFORMATION: Luciferase antisense

<400> SEQUENCE: 8
gcgcugcugg ugccaaccct t                                              21

<210> SEQ ID NO 9
<211> LENGTH: 21
<212> TYPE: DNA
<213> ORGANISM: Artificial Sequence
<220> FEATURE:
<223> OTHER INFORMATION: Luciferase antisense

<400> SEQUENCE: 9
ggguuggcac cagcagcgct t                                              21

<210> SEQ ID NO 10
<211> LENGTH: 22
<212> TYPE: DNA
<213> ORGANISM: Artificial Sequence
<220> FEATURE:
<223> OTHER INFORMATION: CD31 Forward

<400> SEQUENCE: 10
cagagcggat aattgccatt cc                                             22

<210> SEQ ID NO 11
<211> LENGTH: 25
<212> TYPE: DNA
<213> ORGANISM: Artificial Sequence
<220> FEATURE:
<223> OTHER INFORMATION: CD31 reverse

<400> SEQUENCE: 11
acaggatgga aatcacaact tcatc                                          25

<210> SEQ ID NO 12
<211> LENGTH: 26
<212> TYPE: DNA
<213> ORGANISM: Artificial Sequence
<220> FEATURE:
<223> OTHER INFORMATION: CD31 probe

<400> SEQUENCE: 12
accctcagga tctcgctgaa caccgc                                         26

<210> SEQ ID NO 13
<211> LENGTH: 22
<212> TYPE: DNA
<213> ORGANISM: Artificial Sequence
<220> FEATURE:

```
<223> OTHER INFORMATION: CD34 Forward

<400> SEQUENCE: 13
tctgcctgga actaagtgaa gc                                              22

<210> SEQ ID NO 14
<211> LENGTH: 21
<212> TYPE: DNA
<213> ORGANISM: Artificial Sequence
<220> FEATURE:
<223> OTHER INFORMATION: CD34 Reverse

<400> SEQUENCE: 14
cctcagactg ggctagaagc a                                               21

<210> SEQ ID NO 15
<211> LENGTH: 25
<212> TYPE: DNA
<213> ORGANISM: Artificial Sequence
<220> FEATURE:
<223> OTHER INFORMATION: CD34 Probe

<400> SEQUENCE: 15
accagcatca gcctcagcct cctcc                                           25
```